(12) United States Patent
Chun et al.

(10) Patent No.: US 11,775,114 B2
(45) Date of Patent: Oct. 3, 2023

(54) DISPLAY DEVICE AND OPERATING METHOD THEREOF

(71) Applicant: Samsung Display Co., LTD., Yongin-si (KR)

(72) Inventors: Seungwook Chun, Daegu (KR); Yuna Kim, Seoul (KR); Soojung Lee, Suwon-si (KR); Boram Choi, Anyang-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

(21) Appl. No.: 17/706,900

(22) Filed: Mar. 29, 2022

(65) Prior Publication Data
US 2022/0404928 A1 Dec. 22, 2022

(30) Foreign Application Priority Data

Jun. 17, 2021 (KR) .................. 10-2021-0078963

(51) Int. Cl.
*G06F 3/041* (2006.01)
*A61B 5/00* (2006.01)
*G01N 27/60* (2006.01)

(52) U.S. Cl.
CPC .......... *G06F 3/0418* (2013.01); *A61B 5/443* (2013.01); *G06F 3/0412* (2013.01); *G01N 27/605* (2013.01); *G06F 2203/04106* (2013.01)

(58) Field of Classification Search
CPC ........ G06F 3/0418; G06F 2203/04106; G06F 3/0412; A61B 5/443; G01N 27/605
See application file for complete search history.

(56) References Cited

U.S. PATENT DOCUMENTS

| | | | |
|---|---|---|---|
| 8,421,775 B2 | 4/2013 | Kim et al. | |
| 9,086,771 B2 | 7/2015 | Pyo et al. | |
| 9,275,611 B2 | 3/2016 | Kim | |
| 2013/0066170 A1* | 3/2013 | Mattoli | A61B 5/0077 600/306 |
| 2016/0274726 A1* | 9/2016 | Chung | G06F 3/014 |

FOREIGN PATENT DOCUMENTS

| | | |
|---|---|---|
| KR | 10-0975869 | 8/2010 |
| KR | 10-1116621 | 3/2012 |
| KR | 10-1617143 | 5/2016 |
| KR | 10-1661454 | 9/2016 |

\* cited by examiner

*Primary Examiner* — Peter D McLoone
(74) *Attorney, Agent, or Firm* — H.C. Park & Associates, PLC

(57) ABSTRACT

A display device including a display panel that displays an image, an input sensor disposed on the display panel, and a readout circuit that receives sensing signals from the input sensor and outputs a moisture level signal, in a skin measurement mode. The readout circuit divides the input sensor into a plurality of blocks, selects a valid sensing block based on the sensing signals from the plurality of blocks, and outputs the moisture level signal based on the sensing signals from the valid sensing block.

16 Claims, 15 Drawing Sheets

FIG. 3
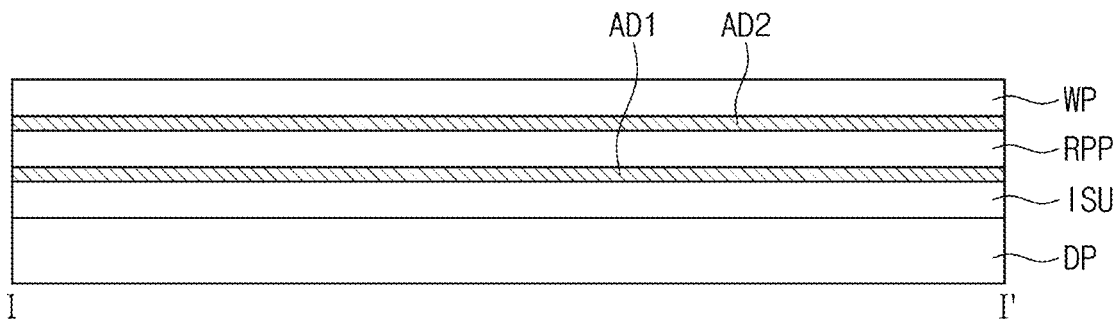
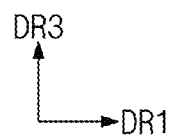
FIG. 4
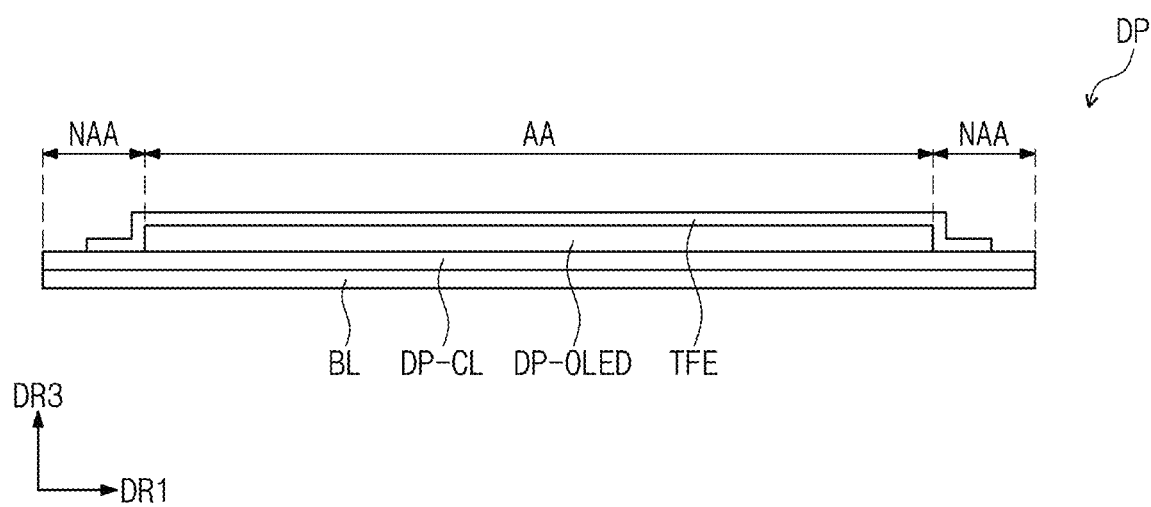

FIG. 12

DISPLAY DEVICE AND OPERATING METHOD THEREOF

CROSS-REFERENCE TO RELATED APPLICATIONS

This application claims priority from and the benefit of Korean Patent Application No. 10-2021-0078963, filed on Jun. 17, 2021, which is hereby incorporated by reference for all purposes as if fully set forth herein.

BACKGROUND

Field

Embodiments of the invention relate generally to a display device.

Discussion of the Background

Multimedia electronic devices such as a TV, a mobile phone, a tablet personal computer (PC), a computer, a navigation device, a game console, and the like include a display device that displays an image. In addition to a general input method such as a button, a keyboard, a mouse, or the like, an electronic device may include a display device capable of providing a touch-based input method that allows a user to enter information or commands easily and intuitively.

Currently, as personal electronic devices such as mobile phones are used widely, there is an increasing need for the display device capable of providing biometric information.

The above information disclosed in this Background section is only for understanding of the background of the inventive concepts, and, therefore, it may contain information that does not constitute prior art.

SUMMARY

Embodiments of the inventive concepts are capable of providing a display device that detects a user's biometric information and provides information about a skin moisture level and an operating method thereof.

Additional features of the inventive concepts will be set forth in the description that follows, and in part will be apparent from the description, or may be learned by practice of the inventive concepts.

According to an embodiment, a display device includes a display panel that displays an image, an input sensor disposed on the display panel, and a readout circuit that receives sensing signals from the input sensor and outputs a moisture level signal, in a skin measurement mode. The readout circuit divides the input sensor into a plurality of blocks, selects a valid sensing block based on the sensing signals from the plurality of blocks, and outputs the moisture level signal based on the sensing signals from the valid sensing block.

In an embodiment, the readout circuit may include an analog-to-digital converter that converts the sensing signals into digital sensing signals, a valid sensing signal selector that selects the valid sensing block among the plurality of blocks based on the digital sensing signals and area information and outputs a valid sensing signal based on the sensing signals from the valid sensing block, an area compensation unit that calculates a touch area based on the digital sensing signals and outputs a compensation signal obtained by performing capacitance compensation according to the touch area on the valid sensing signal, and a moisture level calculator that outputs the moisture level signal based on the compensation signal.

In an embodiment, the valid sensing signal selector may select touch blocks, from each of which a touch of a user is detected, from among the plurality of blocks, may calculate a representative value of each of the touch blocks, and a mean of representative values of the touch blocks, and may select the valid sensing block based on the representative values of the touch blocks, and the mean.

In an embodiment, the representative value may be one of a mean, a median, and a mode of the compensation signal in the valid sensing block.

In an embodiment, the valid sensing signal selector may select one of the touch blocks which has the greatest difference value between the mean and each of the representative values of the touch blocks, as the valid sensing block.

In an embodiment, the display device may further include a memory that stores the area information of the input sensor.

In an embodiment, the input sensor may be disposed on the display panel. The input sensor may include first sensing electrodes, second sensing electrodes crossing the first sensing electrodes, first signal lines respectively connected to the first sensing electrodes, and second signal lines respectively connected to the second sensing electrodes.

In an embodiment, the readout circuit may transmit a transmission signal to the first signal lines and may receive the sensing signals from the second signal lines.

In an embodiment, the first sensing electrodes and the second sensing electrodes have a mesh shape.

In an embodiment, the readout circuit may include a transmitter that provides transmission signals to the first signal lines, a receiver that receives the sensing signals from the second signal lines, and a control circuit. The control circuit may control the transmitter and the receiver and may include the analog-to-digital converter, the valid sensing signal selector, the area compensation unit, and the moisture level calculator.

In an embodiment, each of the sensing signals may be representative of a capacity between one of the first sensing electrodes and one of the second sensing electrodes.

In an embodiment, the touch area may be proportional to the number of digital sensing signals, each of which exceeds a reference level, from among the digital sensing signals output from the analog-to-digital converter.

According to an embodiment, a display device includes a display panel that displays an image, an input sensor disposed on the display panel and which includes first sensing electrodes and second sensing electrodes electrically isolated from the first sensing electrodes, and a readout circuit connected to the input sensor. The readout circuit divides the input sensor into a plurality of blocks, selects a valid sensing block based on the sensing signals from the first sensing electrodes of the plurality of blocks and outputs a moisture level signal based on the sensing signals from the valid sensing block.

In an embodiment, the display device may further include an analog-to-digital converter that converts the sensing signals into digital sensing signals, a valid sensing signal selector that selects the valid sensing block among the plurality of blocks based on the digital sensing signals and area information and outputs a valid sensing signal based on the sensing signals from the valid sensing block, an area compensation unit that calculates a touch area based on the digital sensing signals and outputs a compensation signal obtained by performing capacitance compensation according to the touch area on the valid sensing signal, and a moisture level calculator that outputs the moisture level signal based on the compensation signal.

In an embodiment, the valid sensing signal selector may select touch blocks, from each of which a touch of a user is detected, from among the plurality of blocks, may calculate a representative value of each of the touch blocks, and a mean of representative values of the touch blocks, and may select the valid sensing block based on the representative values of the touch blocks and the mean.

In an embodiment, the representative value may be one of a mean, a median, and a mode of the compensation signal in the valid sensing block.

According to an embodiment, an operating method of a display device which includes a display panel and an input sensor includes dividing the input sensor into a plurality of blocks, receiving sensing signals from the input sensor, generating touch raw data based on the sensing signals, selecting a valid sensing block among the plurality of blocks based on the touch raw data and outputting the touch raw data of the valid sensing block as a valid sensing signal, calculating a touch area based on the touch raw data and outputting a compensation signal obtained by compensating for capacitance of the valid sensing signal depending on the touch area, outputting a moisture level signal based on the compensation signal, and displaying an image corresponding to the moisture level signal on the display panel.

In an embodiment, the selecting of the valid sensing signal may include selecting blocks, from each of which a touch of a user is detected, from among the plurality of blocks, calculating a representative value of each of the blocks, from each of which the touch of the user is detected, and a mean of representative values of the blocks, from each of which the touch of the user is detected, selecting the valid sensing block based on the representative values of the blocks, from each of which the touch of the user is detected, and the mean, and outputting the touch raw data of the valid sensing block as the valid sensing signal.

In an embodiment, the representative value may be one of a mean, a median, and a mode of the compensation signal in the valid sensing block.

In an embodiment, the input sensor may be disposed on the display panel. The input sensor may include first sensing electrodes, second sensing electrodes crossing the first sensing electrodes, first signal lines respectively connected to the first sensing electrodes, and second signal lines respectively connected to the second sensing electrodes.

It is to be understood that both the foregoing general description and the following detailed description are illustrative and explanatory and are intended to provide further explanation of the invention as claimed.

BRIEF DESCRIPTION OF THE FIGURES

The accompanying drawings, which are included to provide a further understanding of the invention and are incorporated in and constitute a part of this specification, illustrate illustrative embodiments of the invention, and together with the description serve to explain the inventive concepts.

FIG. 3 is a cross-sectional view of a display device taken along line I-I' illustrated in FIG. 2.

FIG. 4 is a cross-sectional view of a display panel shown in FIG. 3.

FIG. 12 is a diagram illustrating a part of digital sensing signals output from an analog-to-digital converter illustrated in FIG. 10.

DETAILED DESCRIPTION

Figure 1:
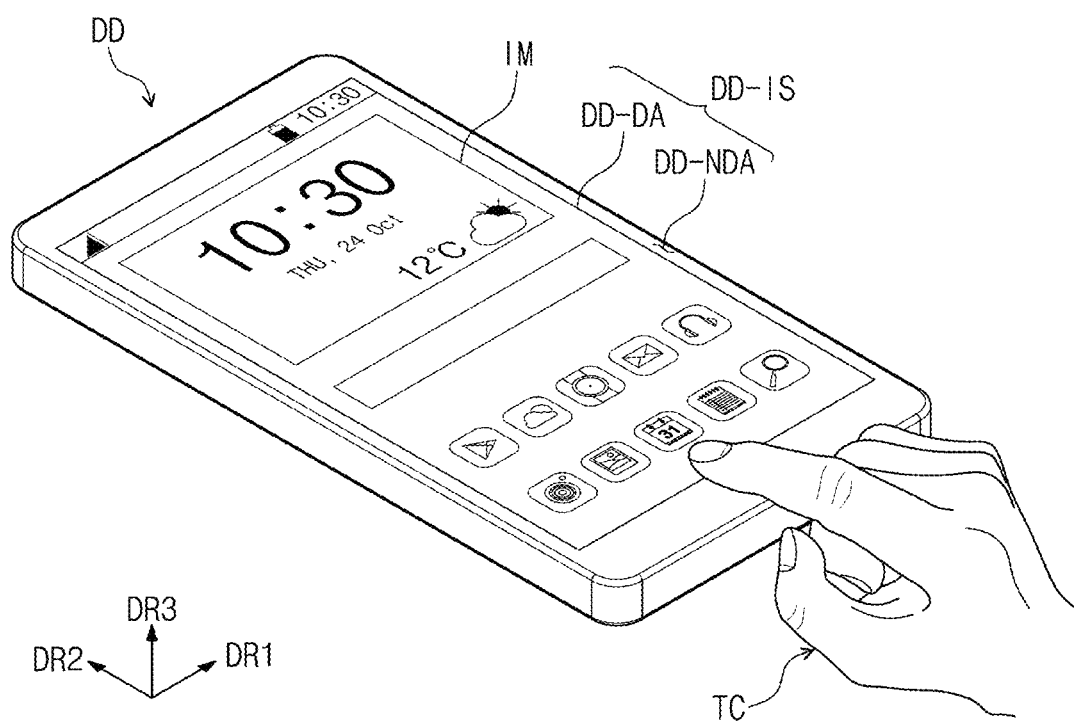
FIG. 1 is a perspective view of a display device, according to an embodiment.

In the following description, for the purposes of explanation, numerous specific details are set forth in order to provide a thorough understanding of various embodiments or implementations of the invention. As used herein "embodiments" and "implementations" are interchangeable words that are non-limiting examples of devices or methods employing one or more of the inventive concepts disclosed herein. It is apparent, however, that various embodiments may be practiced without these specific details or with one or more equivalent arrangements. In other instances, well-known structures and devices are shown in block diagram form in order to avoid unnecessarily obscuring various embodiments. Further, various embodiments may be different, but do not have to be exclusive. For example, specific shapes, configurations, and characteristics of an embodiment may be used or implemented in another embodiment without departing from the inventive concepts.

Unless otherwise specified, the illustrated embodiments are to be understood as providing features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the DR1-axis, the DR2-axis, and the DR3-axis are not limited to three axes of a rectangular coordinate system, such as the x, y, and z-axes, and may be interpreted in a broader sense. For example, the DR1-axis, the DR2-axis, and the DR3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various embodiments are described herein with reference to sectional and/or exploded illustrations that are schematic illustrations of idealized embodiments and/or intermediate structures. As such, variations from the shapes of the illustrations as a result, for example, of manufacturing techniques and/or tolerances, are to be expected. Thus, embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

As is customary in the field, some embodiments are described and illustrated in the accompanying drawings in terms of functional blocks, units, and/or modules. Those skilled in the art will appreciate that these blocks, units, and/or modules are physically implemented by electronic (or optical) circuits, such as logic circuits, discrete components, microprocessors, hard-wired circuits, memory elements, wiring connections, and the like, which may be formed using semiconductor-based fabrication techniques or other manufacturing technologies. In the case of the blocks, units, and/or modules being implemented by microprocessors or other similar hardware, they may be programmed and controlled using software (e.g., microcode) to perform various functions discussed herein and may optionally be driven by firmware and/or software. It is also contemplated that each block, unit, and/or module may be implemented by dedicated hardware, or as a combination of dedicated hardware to perform some functions and a processor (e.g., one or more programmed microprocessors and associated circuitry) to perform other functions. Also, each block, unit, and/or module of some embodiments may be physically separated into two or more interacting and discrete blocks, units, and/or modules without departing from the scope of the inventive concepts. Further, the blocks, units, and/or modules of some embodiments may be physically combined into more complex blocks, units, and/or modules without departing from the scope of the inventive concepts.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

Hereinafter, various embodiments of the inventive concepts will be described with reference to accompanying drawings.

FIG. 1 is a perspective view of a display device DD, according to an embodiment.

As illustrated in FIG. 1, the display device DD may display an image IM through a display surface DD-IS. The display surface DD-IS is parallel to a surface defined by a first direction axis DR1 and a second direction axis DR2. A normal direction of the display surface DD-IS, that is, a thicknesses direction of the display device DD corresponds to a third direction axis DR3.

A front surface (or an upper surface) and a back surface (or a lower surface) of each part or member described later are divided by the third direction axis DR3. However, the first to third direction axes DR1, DR2, and DR3 illustrated in an embodiment are only examples. Hereinafter, first to third directions are defined as directions indicated by the first, second, and third direction axes DR1, DR2, and DR3, respectively. The first to third directions are marked by the same reference symbols.

The display device DD including a flat display surface is illustrated in an embodiment. However, the embodiment described herein is not limited thereto. The display device DD may further include a curved display surface. The display device DD may include a three-dimensional (3D) display surface. The 3D display surface may include a plurality of display areas facing in different directions, respectively. For example, the 3D display surface may include a polygonal columnar display surface.

The display device DD according to an embodiment may be a rigid display device. However, the embodiments described herein are not limited thereto. For example, the display device DD according to an embodiment may be a flexible display device. The flexible display device may include a foldable display device, a bending-type display device where a partial area is bent, or a slidable display device.

In an embodiment, FIG. 1 illustrates the display device DD that is applicable to a mobile phone terminal. According to an embodiment, the display device DD may be applied to a small and medium-sized electronic device, such as a tablet PC, a vehicle navigation system, a game console, a smart watch, or the like as well as a large-sized electronic device, such as a television, a monitor, or the like.

As illustrated in FIG. 1, the display surface DD-IS includes an image area DD-DA, in which the image IM is displayed, and a bezel area DD-NDA adjacent to the image area DD-DA. The bezel area DD-NDA refers to an area where an image is not displayed. FIG. 1 illustrates a clock and icon images as an example of the image IM.

As illustrated in FIG. 1, the image area DD-DA may have a substantially-rectangular shape. The "substantially-rectangular shape" includes not only a rectangular shape defined mathematically, but also a rectangular shape in which a boundary of a curve is defined without defining a vertex in a vertex area (or a corner area).

The bezel area DD-NDA may surround the image area DD-DA. However, the present disclosure is not limited thereto. For example, the image area DD-DA and the bezel area DD-NDA may be designed in different shapes. The bezel area DD-NDA may be disposed on only one side of the image area DD-DA. The bezel area DD-NDA may not be exposed to the outside depending on the coupled shape of the display device DD and another component of an electronic device.

The display device DD according to an embodiment may detect an externally-applied user input TC. The user input TC may be one or a combination of various external inputs such as a part of the user's body, a tool such as a stylus pen, and the like. The display device DD may detect the user input TC by detecting a change in one of reflection light, temperature, pressure, ultrasonic wave, or electromagnetic field, or a combination thereof in response to the user input TC. In an embodiment, it is assumed that the user input TC is a touch input by a user's hand applied to a front surface of the display device DD, but an input scheme of the user input TC is an example. As described above, the user input TC may be provided in various input schemes. Besides, the display device DD may detect the user input TC applied to a side surface or a rear surface of the display device DD depending on a structure of the display device DD, and may not be limited to an embodiment.

Figure 2:
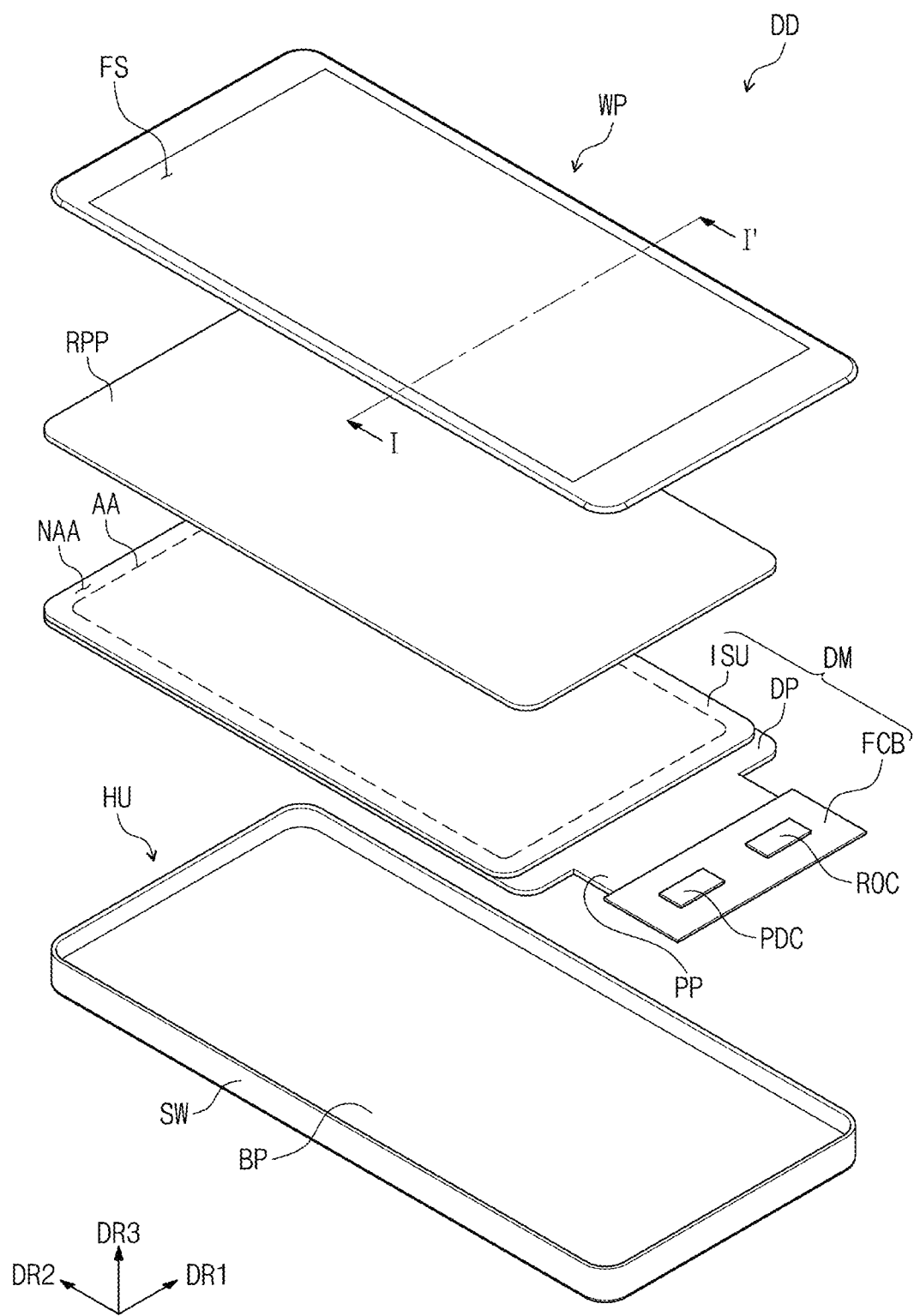
FIG. 2 is an exploded perspective view of a display device, according to an embodiment.

FIG. 2 is an exploded perspective view of a display device, according to an embodiment.

Referring to FIG. 2, the display device DD may include a window WP, an anti-reflection panel RPP, a display module DM, and housing HU. As illustrated in FIGS. 1 and 2, in an embodiment, an appearance of the display device DD may be formed by coupling the window WP and the housing HU.

The window WP protects an upper surface of a display panel DP. The window WP may include an optically transparent insulating material. For example, the window WP may include a front surface FS including glass or plastic. The window WP may include a multi-layer structure or a single-layer structure. For example, the window WP may include a plurality of plastic films bonded through an adhesive or may include a glass substrate and a plastic film that are bonded through an adhesive.

The anti-reflection panel RPP may be disposed under the window WP. The anti-reflection panel RPP reduces a reflectance of external light incident from an upper surface of the window WP. In an embodiment, the anti-reflection panel RPP may be omitted or may be embedded in the display module DM.

The display module DM may display the image IM and may detect an external input. The display module DM may include the display panel DP, an input sensor ISU, and a printed circuit board FCB.

An active area AA corresponding to the image area DD-DA illustrated in FIG. 1 and a peripheral area NAA corresponding to the bezel area DD-NDA illustrated in FIG. 1 may be defined in the display panel DP. The display panel DP may be a configuration that substantially generates the image IM. The image IM generated in the active area AA of the display panel DP is visibly perceived by a user from the outside through the window WP.

The input sensor ISU detects the external input applied from the outside. As described above, the input sensor ISU may detect an external input provided to the window WP.

The display panel DP may include a pad area PP. A plurality of signal pads DP-PD and IS-PD (refer to FIG. 5) may be disposed in the pad area PP of the display panel DP. The display panel DP may be electrically connected to the printed circuit board FCB through pads.

The printed circuit board FCB may include various driving circuits that drive the display panel DP and the input sensor ISU, a connector for power supply, or the like. In an embodiment, the printed circuit board FCB may include a panel driving circuit PDC that drives the display panel DP, and a readout circuit ROC that drives the input sensor ISU. Each of the panel driving circuit PDC and the readout circuit ROC may be formed as an integrated circuit and may be mounted on the printed circuit board FCB. In an embodiment, the panel driving circuit PDC and the readout circuit ROC may be integrated with one integrated circuit.

The housing HU includes a bottom part BP and a side wall SW. The side wall SW may be extended from the bottom part BP. The housing HU may accommodate the display panel DP in the accommodation space defined by the bottom part BP and the side wall SW. The window WP may be coupled with the side wall SW of the housing HU. The side wall SW of the housing HU may support an outer portion of the window WP.

The housing HU may include a material having relatively high rigidity. For example, the housing HU may include glass, plastic, or metal or may include a plurality of frames and/or a plurality of plates composed of a combination thereof. The housing HU may stably protect configurations of the display device DD accommodated in the inner space from an external impact.

FIG. 3 is a cross-sectional view of a display device taken along line I-I' illustrated in FIG. 2.

FIG. 3 illustrates a cross section of the display device DD defined by the first direction axis DR1 and the third direction axis DR3. FIG. 3 illustrates components of the display device DD simply to explain a stacked relationship between the components.

According to an embodiment, the display device DD may include the display panel DP, the input sensor ISU, the anti-reflection panel RPP, and the window WP. At least part of components among the display panel DP, the input sensor ISU, the anti-reflection panel RPP, and the window WP may be formed in successive processes. Alternatively, at least part of the components thereof may be coupled with one another by an adhesive member. For example, the input sensor ISU and the anti-reflection panel RPP may be coupled with each other by an adhesive member AD1. The anti-reflection panel RPP and the window WP may be coupled with each other by an adhesive member AD2.

Each of the adhesive members AD1 and AD2 may refer to a transparent adhesive member such as a pressure sensitive adhesive (PSA) film, an optically clear adhesive (OCA) film, or an optically clear resin (OCR). An adhesive member described later may include a general adhesive or a pressure sensitive adhesive. In an embodiment, the anti-reflection panel RPP and the window WP may be replaced with other components or may be omitted in some implementations of the embodiment.

In FIG. 3, the input sensor ISU, which is formed through successive processes together with the display panel DP, from among the input sensor ISU, the anti-reflection panel (anti-reflector) RPP, and the window WP is directly disposed on the display panel DP. In this specification, "component B is directly disposed on component A" denotes that a separate adhesive layer/member is not interposed between component A and component B. Component B is formed on a base surface, which is provided by component A after component A is formed, through successive processes.

In an embodiment, each of the anti-reflection panel RPP and the window WP has a "panel" type, and the input sensor ISU has a "layer" type. A component of the "panel" type includes a base layer providing a base surface, such as a synthetic resin film, a composite film, a glass substrate, or the like. However, the base layer may be omitted in a component of the "layer" type in some implementations of the embodiment. In other words, components of the "layer" type are disposed on the base surface provided by another component. In an embodiment, the anti-reflection panel RPP and the window WP may have the "layer" type.

The display panel DP generates an image, and the input sensor ISU obtains coordinate information of an external input (e.g., a touch event). Although not separately illustrated in FIG. 3, the display device DD according to an embodiment may further include a protective member disposed on a lower surface (or a bottom surface) of the display panel DP. The protective member and the display panel DP may be bonded through an adhesive member.

The display panel DP according to an embodiment may be a light emitting display panel, but is not particularly limited thereto. For example, the display panel DP may be an organic light emitting display panel or a quantum dot light emitting display panel. The panels are distinguished from one another depending on a material of a light emitting element. A light emitting layer of the organic light emitting display panel may include an organic light emitting material. A light emitting layer of the quantum dot light emitting display panel may include a quantum dot and/or a quantum rod. Hereinafter, it is described that the display panel DP is an organic light emitting display panel.

The anti-reflection panel RPP reduces a reflectance of external light incident from an upper surface of the window WP. The anti-reflection panel RPP according to an embodiment may include a retarder and a polarizer. The retarder may have a film type or a liquid crystal coating type. The polarizer may also have a film type or liquid crystal coating type. A panel of the film type may include a stretched synthetic resin film, and a panel of the liquid crystal coating type may include liquid crystals arranged in a predetermined array. Each of the retarder and the polarizer may further include a protective film. The retarder and polarizer themselves may be defined as a base layer of the anti-reflection panel RPP. Alternatively, the protective film may be defined as the base layer of the anti-reflection panel RPP.

The anti-reflection panel RPP according to an embodiment may include color filters. The color filters have a predetermined array. An array of color filters may be determined in consideration of light emitting colors of pixels included in the display panel DP. The anti-reflection panel RPP may further include a black matrix adjacent to the color filters.

The anti-reflection panel RPP according to an embodiment may include a destructive interference structure. For example, the destructive interference structure may include a first reflective layer and a second reflective layer, which are disposed on different layers from each other. First reflected light and second reflected light, which are respectively reflected from the first reflective layer and the second reflective layer, may destructively interfere with each other, thereby reducing the reflectance of external light.

The window WP according to an embodiment may include a glass substrate and/or a synthetic resin film. The window WP is not limited to a single layer. The window WP may include two or more films that are bonded with one another through an adhesive member. Although not separately illustrated in drawings, the window WP may further include a functional coating layer. The functional coating layer may include an anti-fingerprint layer, an anti-reflection layer, a hard coating layer, and the like.

The input sensor ISU and the display panel DP will be described in detail later.

FIG. 4 is a cross-sectional view of the display panel DP shown in FIG. 3.

As illustrated in FIG. 4, the display panel DP includes a base layer BL, a circuit element layer DP-CL disposed on the base layer BL, a light emitting element layer DP-OLED, and a thin film encapsulation layer TFE. The active area AA corresponding to the image area DD-DA illustrated in FIG. 1 and the peripheral area NAA corresponding to the bezel area DD-NDA illustrated in FIG. 1 may be defined in the display panel DP. In this specification, "a region/portion corresponds to another region/portion" denotes "a region/portion overlaps another region/portion", but is not limited to having the same area and/or the same shape.

The base layer BL may include at least one synthetic resin film. The base layer BL may include a glass substrate, a metal substrate, or an organic/inorganic composite substrate.

The circuit element layer DP-CL is disposed on the base layer BL. The circuit element layer DP-CL includes at least one insulating layer and circuit elements. The insulating layer includes at least one inorganic layer and at least one organic layer. The circuit elements may include signal lines, a pixel driving circuit, and the like.

The light emitting element layer DP-OLED is disposed on the circuit element layer DP-CL. The light emitting element layer DP-OLED includes organic light emitting diodes as light emitting elements. The light emitting element layer DP-OLED may further include an organic layer such as a pixel defining film.

The thin film encapsulation layer TFE may be disposed on the light emitting element layer DP-OLED so as to encapsulate the light emitting element layer DP-OLED. The thin film encapsulation layer TFE may overall cover the active area AA. The thin film encapsulation layer TFE may cover a part of the peripheral area NAA.

The thin film encapsulation layer TFE includes a plurality of thin films. A part of thin films are disposed to improve optical efficiency. The other parts of thin films are disposed to protect organic light emitting diodes.

Figure 5:
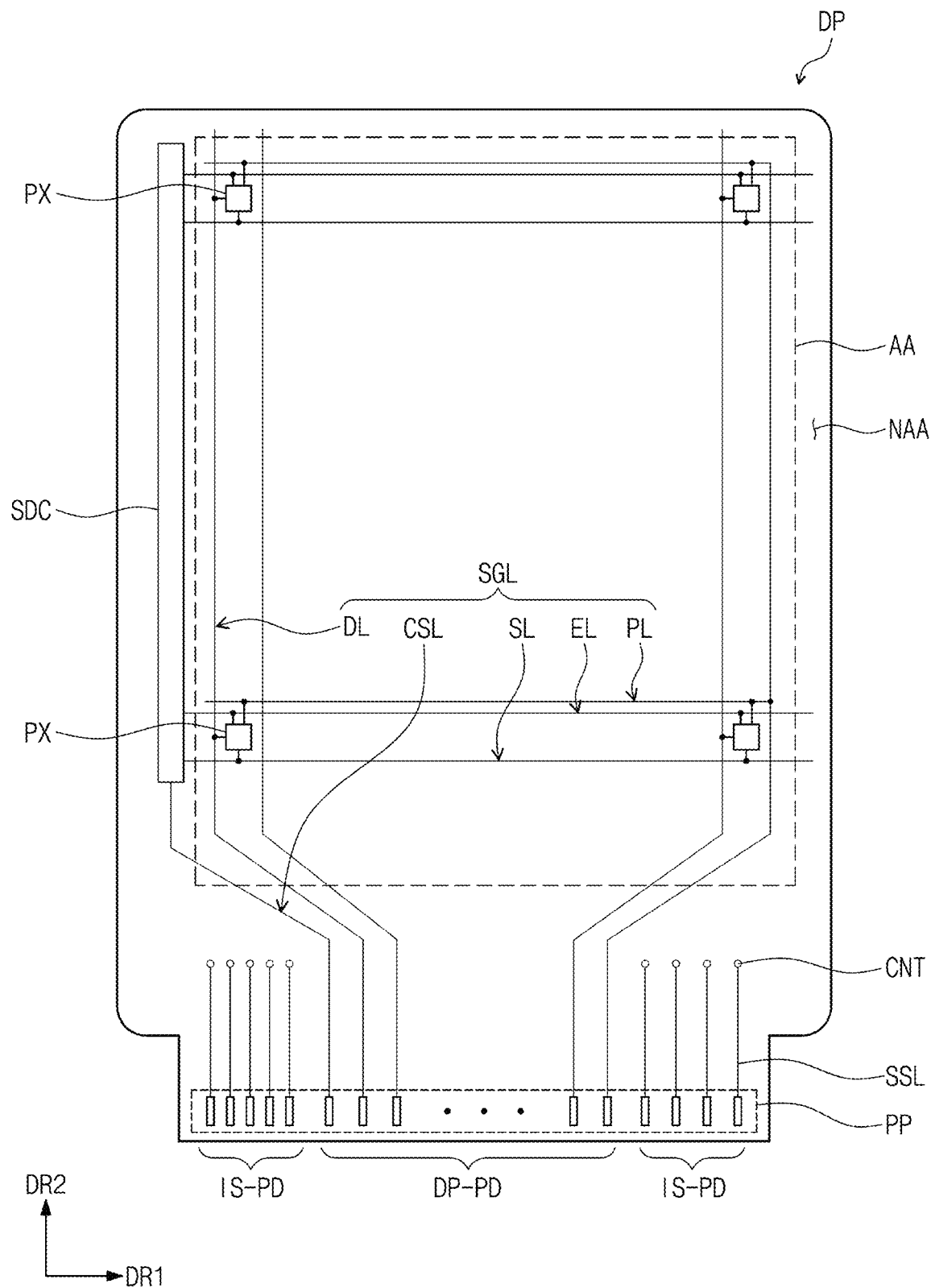
FIG. 5 is a plan view of a display panel according to an embodiment.

FIG. 5 is a plan view of the display panel DP, according to an embodiment.

As illustrated in FIG. 5, the display panel DP may include a scan driving circuit SDC, a plurality of signal lines SGL (hereinafter referred to as "signal lines"), the plurality of signal pads DP-PD and IS-PD (hereinafter referred to as "signal pads"), and a plurality of pixels PX (hereinafter referred to as "pixels").

The scan driving circuit SDC generates a plurality of scan signals (hereinafter referred to as "scan signals") and sequentially outputs the scan signals to a plurality of scan lines SL (hereinafter referred to as "scan lines") to be described later. The scan driving circuit SDC may output not only the scan signals but also other control signals to the pixels PX.

The scan driving circuit SDC may include a plurality of transistors formed through the same process as a process in which transistors in the pixels PX are formed.

The signal lines SGL may include the scan lines SL, data lines DL, a power supply line PL, light emitting control lines EL, and a control signal line CSL. Each of the scan lines SL is connected to the corresponding pixel PX among the pixels PX; each of the data lines DL is connected to the corresponding pixel PX among the pixels PX; and, each of the light emitting control lines EL is connected to the corresponding pixel PX among the pixels PX. The power supply line PL is connected in common with the pixels PX. The control signal line CSL may provide control signals to the scan driving circuit SDC. The power supply line PL may provide a voltage necessary for operations of the pixels PX. The power supply line PL may include a plurality of lines that provide different voltages from one another.

In an embodiment, the signal lines SGL may further include auxiliary lines SSL. Each of the auxiliary lines SSL refers to a signal line connected to the input sensor ISU (refer to FIG. 2). In an embodiment, the auxiliary lines SSL may be omitted. The auxiliary lines SSL are connected to contact holes CNT, respectively. The auxiliary lines SSL may be electrically connected to signal lines of the input sensor ISU (refer to FIG. 6) described later through the contact holes CNT.

The signal pads DP-PD and the signal pads IS-PD may include first-type signal pads DP-PD connected to the data lines DL, the power supply line PL, and the control signal line CSL and second-type signal pads IS-PD connected to the auxiliary lines SSL. The first-type signal pads DP-PD and the second-type signal pads IS-PD are disposed adjacent to each other in a pad area PP defined in a partial area of the peripheral area NAA. A stacked structure of the signal pads DP-PD is not distinguished from a stacked structure of the signal pads IS-PD; and, materials of the signal pads DP-PD are not distinguished from materials of the signal pads IS-PD. The signal pads DP-PD and the signal pads IS-PD may be formed through the same process as each other.

The active area AA may be defined as an area in which the pixels PX are disposed. A plurality of electronic elements are disposed in the active area AA. The electronic elements include an organic light emitting diode included in each of the pixels PX and a pixel driving circuit connected to the organic light emitting diode. The circuit element layer DP-CL illustrated in FIG. 4 may include the scan driving circuit SDC, the signal lines SGL, the signal pads DP-PD and IS-PD, and the pixel driving circuit.

Each of the pixels PX may include a plurality of transistors, a capacitor, and an organic light emitting diode. The pixels PX emit light in response to signals received through the scan lines SL, the data lines DL, the light emitting control lines EL, and the power supply line PL.

The signal pads DP-PD and IS-PD of the display panel DP may be electrically connected to the printed circuit board FCB illustrated in FIG. 2. That is, the display panel DP may be electrically connected to the panel driving circuit PDC and the readout circuit ROC of the printed circuit board FCB through the signal pads DP-PD and IS-PD.

A part of the display panel DP illustrated in FIG. 4 may be bent. A part of the peripheral area NAA of the display panel DP may be bent and may be bent around a bending axis parallel to the first direction DR1. The bending axis may be defined such that a part of the data lines DL overlaps a part of the auxiliary lines SSL.

Figure 6:
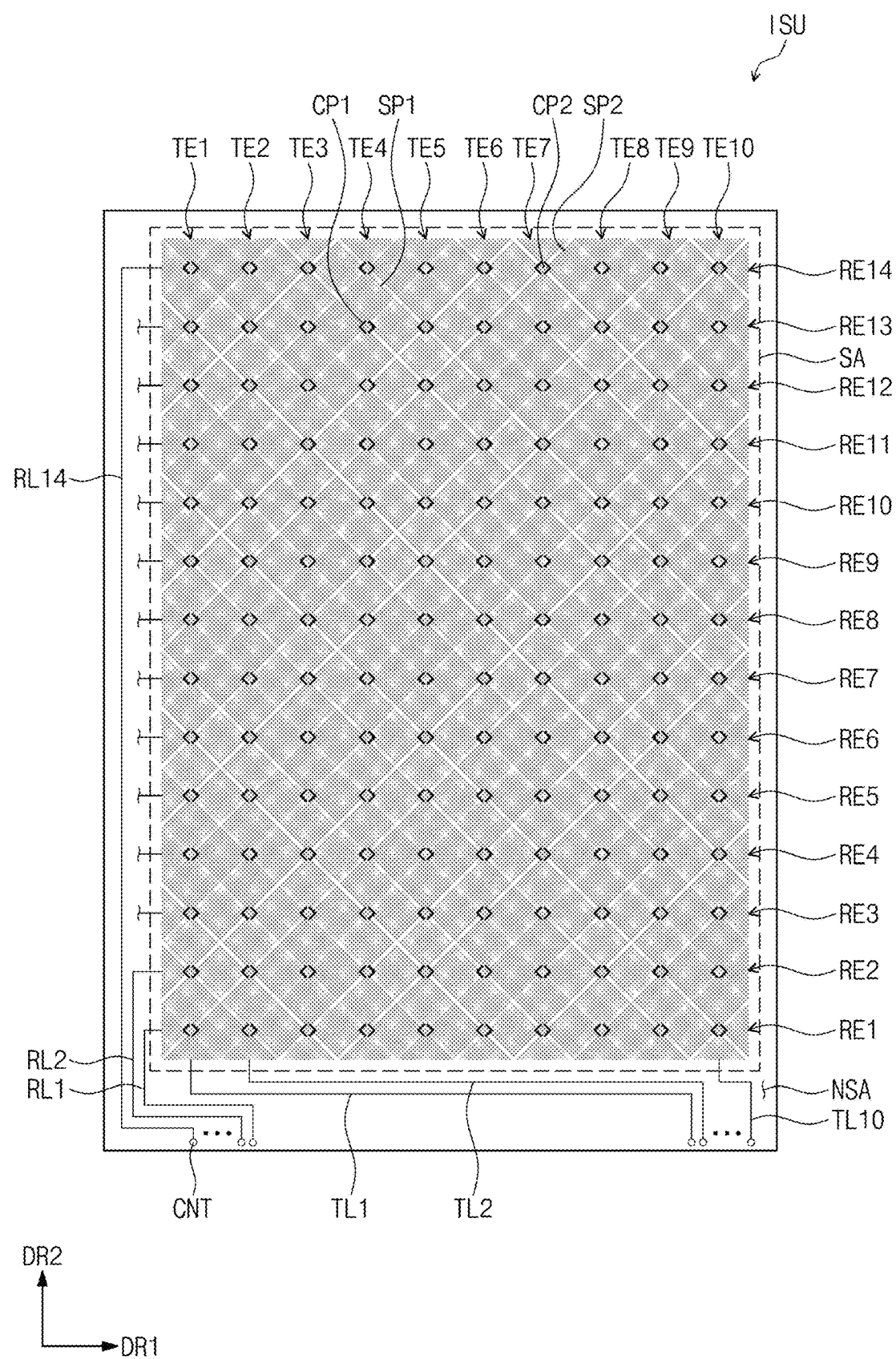
FIG. 6 is a plan view illustrating a configuration of an input sensor, according to an embodiment.

FIG. 6 is a plan view illustrating a configuration of the input sensor ISU, according to an embodiment.

Referring to FIG. 6, the input sensor ISU may include a sensing area SA and a non-sensing area NSA. The sensing area SA may be an area activated depending on an electrical signal. In an embodiment, the sensing area SA may be an area in which an input is sensed. The non-sensing area NSA may surround the sensing area SA. The sensing area SA may correspond to the active area AA of FIG. 5, and the non-sensing area NSA may correspond to the peripheral area NAA of FIG. 5.

The input sensor ISU includes transmission electrodes TE1 to TE10 (or first sensing electrodes) and reception electrodes RE1 to RE14 (or second sensing electrodes). The transmission electrodes TE1 to TE10 and the reception electrodes RE1 to RE14 are arranged in the sensing area SA. The transmission electrodes TE1 to TE10 and the reception electrodes RE1 to RE14 are electrically insulated from each other and cross each other in the sensing area SA. In an embodiment, the input sensor ISU includes the first to tenth transmission electrodes TE1 to TE10 and the first to fourteenth reception electrodes RE1 to RE14, but the present disclosure is not limited thereto. The number of transmission electrodes and the number of reception electrodes may be variously changed. FIG. 6 illustrates that the number of reception electrodes is greater than the number of transmission electrodes. However, in an embodiment, the number of transmission electrodes may not be less than the number of reception electrodes.

In this specification, to clearly distinguish between the electrodes TE1 to TE10 and the electrodes RE1 to RE14, the electrodes TE1 to TE10 are referred to as "transmission electrodes", and the electrodes RE1 to RE14 are referred to as "reception electrodes. However, functions of the electrodes are not limited to the names. Depending on an operating mode, the transmission electrodes TE1 to TE10 may operate as reception electrodes as well as transmission electrodes, and the reception electrodes RE1 to RE14 may operate as transmission electrodes as well as reception electrodes.

Each of the first to tenth transmission electrodes TE1 to TE10 may extend in the second direction DR2. The first to tenth the transmission electrodes TE1 to TE10 may be arranged spaced from each other in the first direction DR1. The first to tenth transmission electrodes TE1 to TE10 may be electrically isolated from each other. Each of the first to tenth transmission electrodes TE1 to TE10 includes first sensing patterns SP1, which are spaced from one another in the first direction DR1, and first connection patterns CP1 electrically connecting the first sensing patterns SP1. The first sensing patterns SP1 and the first connection patterns CP1 are disposed on different layers and do not have any shape.

Each of the first to fourteenth reception electrodes RE1 to RE14 extends in the first direction DR1. The first to fourteenth reception electrodes RE1 to RE14 may be arranged spaced from one another in the second direction DR2. The first to fourteenth reception electrodes RE1 to RE14 may be electrically isolated from each other. The first to fourteenth reception electrodes RE1 to RE14 may be arranged to cross the first to tenth transmission electrodes TE1 to TE10 and electrically insulated from the first to tenth transmission electrodes TE1 to TE10. Each of the first to fourteenth reception electrodes RE1 to RE14 includes second sensing patterns SP2, which are spaced from one another in the first direction DR1, and second connection patterns CP2 electrically connecting the second sensing patterns SP2. The second sensing patterns SP2 and the second connection patterns CP2 may have an integral shape.

FIG. 6 illustrates the first sensing patterns SP1 and the second sensing patterns SP2 having a rhombus shape, but the present disclosure is not limited thereto. The first sensing patterns SP1 and the second sensing patterns SP2 may have different polygonal shapes from one another.

The first to tenth transmission electrodes TE1 to TE10 and the first to fourteenth reception electrodes RE1 to RE14 may be arranged in a mesh shape. As the first to tenth transmission electrodes TE1 to TE10 and the first to fourteenth reception electrodes RE1 to RE14 are arranged in a mesh shape, a parasitic capacitance with electrodes (e.g., a second electrode CE (refer to FIG. 7)) of the display panel DP (refer to FIG. 5) may be reduced.

The input sensor ISU may obtain location information about an external input through a change in mutual capacitance between the first to tenth transmission electrodes TE1 to TE10 and the first to fourteenth reception electrodes RE1 to RE14.

The input sensor ISU may further include first to tenth transmission lines TL1 to TL10 (or first signal lines) and first to fourteenth reception lines RL1 to RL14 (or second signal lines). The first to tenth transmission lines TL1 to TL10 and the first to fourteenth reception lines RL1 to RL14 may be arranged in the non-sensing area NSA. The first to tenth transmission lines TL1 to TL10 are electrically connected to sides of the transmission electrodes TE1 to TE10, respectively. The first to fourteenth reception lines RL1 to RL14 are electrically connected to sides of the reception electrodes RE1 to RE14, respectively. However, the present disclosure is not limited thereto. In an embodiment, the input sensor ISU may further include transmission lines electrically connected to the other sides of the first to tenth transmission electrodes TE1 to TE10, respectively.

One end of each of the first to tenth transmission lines TL1 to TL10 and one end of each of the first to fourteenth reception lines RL1 to RL14 may be electrically connected to the auxiliary lines SSL illustrated in FIG. 5 through the contact hole CNT.

The input sensor ISU is electrically connected to the readout circuit ROC (refer to FIG. 2) through the first to tenth transmission lines TL1 to TL10 and the first to fourteenth reception lines RL1 to RL14. The readout circuit ROC may control an operation of the input sensor ISU.

Figure 7:
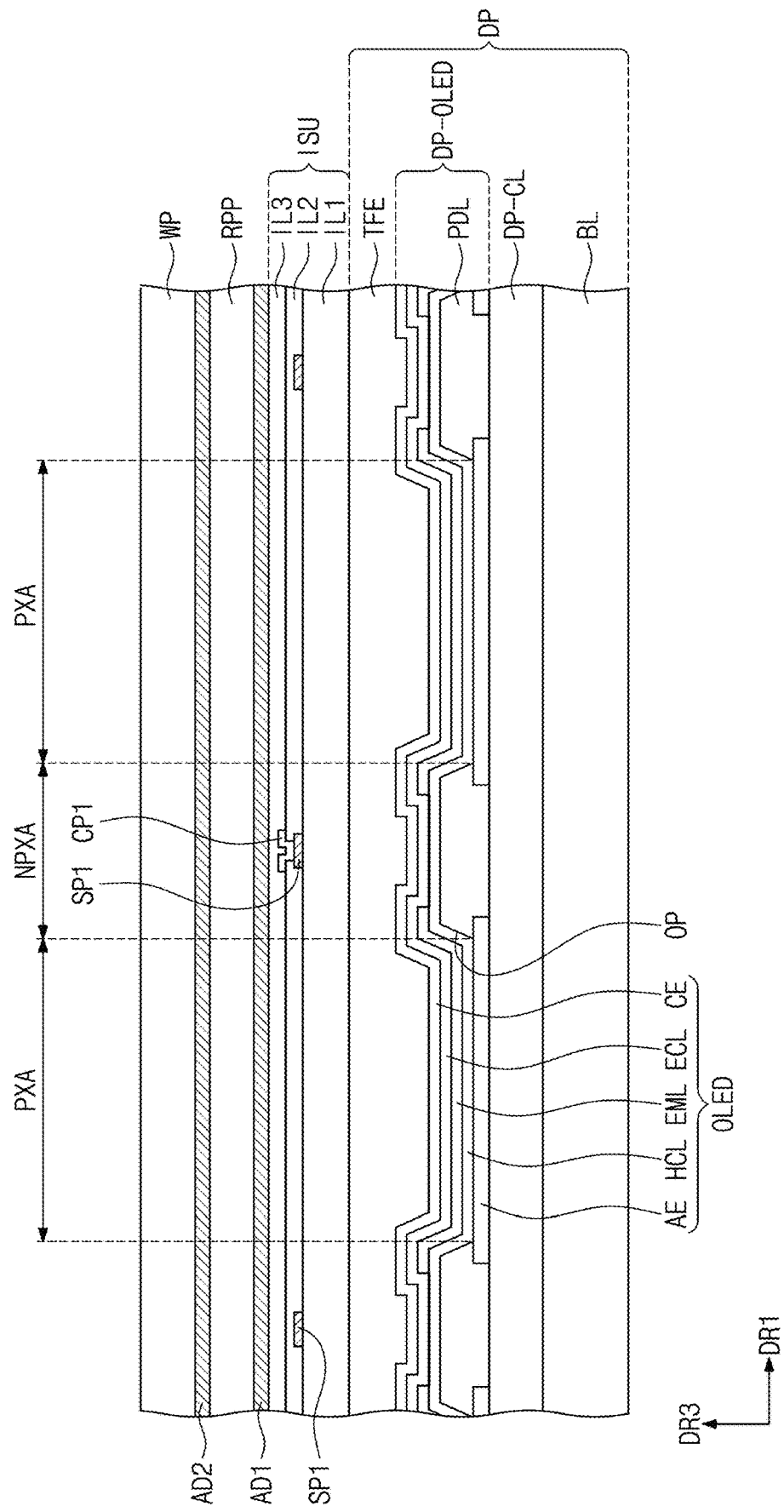
FIG. 7 is a cross-sectional view of a display device, according to an embodiment.

FIG. 7 is a cross-sectional view of a display device according to an embodiment.

As illustrated in FIG. 7, the display panel DP includes the base layer BL, the circuit element layer DP-CL disposed on the base layer BL, the light emitting element layer DP-OLED, and the thin film encapsulation layer TFE. The display panel DP may further include functional layers such as an anti-reflection layer, a refractive-index adjustment layer, and the like.

The base layer BL may include a synthetic resin film. The synthetic resin layer is formed on a working substrate used when the display panel DP is manufactured. Afterward, a conductive layer, an insulating layer, and the like are formed on the synthetic resin layer. When the working substrate is removed, the synthetic resin layer corresponds to the base layer BL. The synthetic resin layer may be a polyimide-based resin layer, and the material thereof is not particularly limited. Besides, the base layer BL may include a glass substrate, a metal substrate, an organic/inorganic composite substrate, or the like.

The circuit element layer DP-CL includes at least one insulating layer and a circuit element. Hereinafter, the insulating layer included in the circuit element layer DP-CL is referred to as an "intermediate insulating layer". The intermediate insulating layer includes at least one intermediate inorganic film and at least one intermediate organic film. The circuit element includes a signal line, a driving circuit of a pixel, and the like. The circuit element layer DP-CL may be formed through a process of forming an insulating layer, a semiconductor layer, and a conductive layer by coating, deposition, or the like, and a patterning process of the insulating layer, the semiconductor layer, and the conductive layer by a photolithography process.

The light emitting element layer DP-OLED may include a pixel defining layer PDL and an organic light emitting diode OLED. The pixel defining layer PDL may include organic materials. A first electrode AE is disposed on the circuit element layer DP-CL. The pixel defining layer PDL is formed on the first electrode AE. An opening OP is defined on the pixel defining layer PDL. The opening OP of the pixel defining layer PDL exposes at least part of the first electrode AE. In an embodiment, the pixel defining layer PDL may be omitted.

A hole control layer HCL may be disposed on the first electrode AE. A light emitting layer EML is disposed on the hole control layer HCL. The light emitting layer EML may be disposed in an area corresponding to the opening OP. That is, the light emitting layer EML may be separately formed on each of pixels PX (refer to FIG. 5). The light emitting layer EML may include an organic material and/or an inorganic material. The light emitting layer EML may generate a predetermined colored light.

An electron control layer ECL is disposed on the light emitting layer EML. The second electrode CE is disposed on the electron control layer ECL. The second electrode CE is disposed in the pixels PX in common.

The thin film encapsulation layer TFE is disposed on the second electrode CE. The thin film encapsulation layer TFE encapsulates the light emitting element layer DP-OLED. The thin film encapsulation layer TFE includes at least one insulating layer. The thin film encapsulation layer TFE according to an embodiment may include at least one inorganic film (hereinafter, referred to as an "encapsulation inorganic film"). The thin film encapsulation layer TFE according to an embodiment may include at least one organic film (hereinafter, referred to as an "encapsulation organic film") and at least one encapsulation inorganic film.

The encapsulation inorganic film protects the light emitting element layer DP-OLED from moisture or oxygen. The encapsulation organic film protects the light emitting element layer DP-OLED from foreign objects such as dust particles. The encapsulation inorganic film may include a silicon nitride layer, a silicon oxynitride layer, a silicon oxide layer, a titanium oxide layer, an aluminum oxide layer, or the like, but not limited thereto. The encapsulation organic film may include an acryl-based organic film, and is not particularly limited thereto.

The input sensor ISU includes a base layer ILL first and second conductive layers disposed on the base layer ILL and first and second insulating layers IL2 and IL3. The base layer IL1 may include an inorganic material, for example, a silicon nitride layer. The inorganic film disposed on the uppermost side of the thin film encapsulation layer TFE may also include silicon nitride. The base layer IL1 and the silicon nitride layer of the thin film encapsulation layer TFE may be formed under different deposition conditions.

A first conductive layer is disposed on the base layer IL1. The first conductive layer may include the first sensing pattern SP1, the second sensing pattern SP2, and the second connection pattern CP2. The second conductive layer is disposed on the first conductive layer. The second conductive layer may include the first connection pattern CP1. The first insulating layer IL2 is interposed between the first conductive layer and the second conductive layer. The first insulating layer IL2 separates the first conductive layer and the second conductive layer on a cross-section. A contact hole for partially exposing the first sensing pattern SP1 may be provided in the first insulating layer IL2. The first connection pattern CP1 may be connected to the first sensing pattern SP1 through the contact hole. The second insulating layer IL3 is disposed on the first insulating layer IL2. The second insulating layer IL3 may cover the second conductive layer. The second insulating layer IL3 protects the second conductive layer from an external environment.

Mesh lines of the first sensing pattern SP1 and the second sensing pattern SP2 may define a plurality of mesh holes. The mesh lines may have a three-layer structure of titanium/aluminum/titanium.

In a display device according to an embodiment, the input sensor ISU may be directly disposed on the display panel DP. In this specification, "being directly disposed" denotes that an adhesive film is not disposed between the input sensor ISU and the display panel DP. That is, the input sensor ISU may be formed on the display panel DP through successive processes. In this case, the input sensor ISU may be expressed as an input sensing layer.

A portion where the first electrode AE and the light emitting layer EML are arranged may be referred to as a "pixel area PXA". The pixel areas PXA may be arranged spaced from one another in each of the first direction DR1 and the second direction DR2 (refer to FIG. 5). A non-pixel area NPXA is interposed between the pixel areas PXA and may surround the pixel areas PXA.

The anti-reflection panel RPP may be disposed on the upper surface of the input sensor ISU. As an example of the use of the anti-reflection panel RPP in the embodiments described herein, the anti-reflection panel RPP may include a polarizing film. The anti-reflection panel RPP may further include a protective film and other functional films in addition to the polarizing film. Hereinafter, only the polarizing film is illustrated for convenience of description. The adhesive member AD1 may be interposed between the anti-reflection panel RPP and the input sensor ISU. Accordingly, the anti-reflection panel RPP may be coupled to the input sensor ISU by the adhesive member AD1. The window WP may be coupled to the anti-reflection panel RPP through the adhesive member AD2.

Retuning to FIG. 6, the input sensor ISU may be a capacitive touch sensor. In an embodiment, one of the first to tenth transmission electrodes TE1 to TE10 and the first to fourteenth reception electrodes RE1 to RE14 receives a transmission signal. Another thereof outputs a capacitance change amount between the first to tenth transmission electrodes TE1 to TE10 and the first to fourteenth reception electrodes RE1 to RE14, as a sensing signal. In an embodiment, when the first transmission electrode TE1 receives a transmission signal (or a drive signal), the first transmission electrode TE1 is capacitively coupled to the first to fourteenth reception electrodes RE1 to RE14. When a part of a user's body is positioned on a specific reception electrode (e.g., the first reception electrode RE1) among the first to fourteenth reception electrodes RE1 to RE14 that are capacitively-coupled, a capacity between the first transmission electrode TE1 and the first reception electrode RE1 is changed. The readout circuit ROC (refer to FIG. 2) may detect the changed capacity of the sensing signal received from the first reception line RL1 connected to the first reception electrode RE1 and then may calculate coordinate information of the user's touch location. In particular, the readout circuit ROC (refer to FIG. 2) according to an embodiment may detect the changed capacity of the sensing signal received from the first to fourteenth reception electrodes RE1 to RE14, and then may detect the user's skin condition (e.g., a skin moisture level (or a skin hydration level)).

Figure 8:
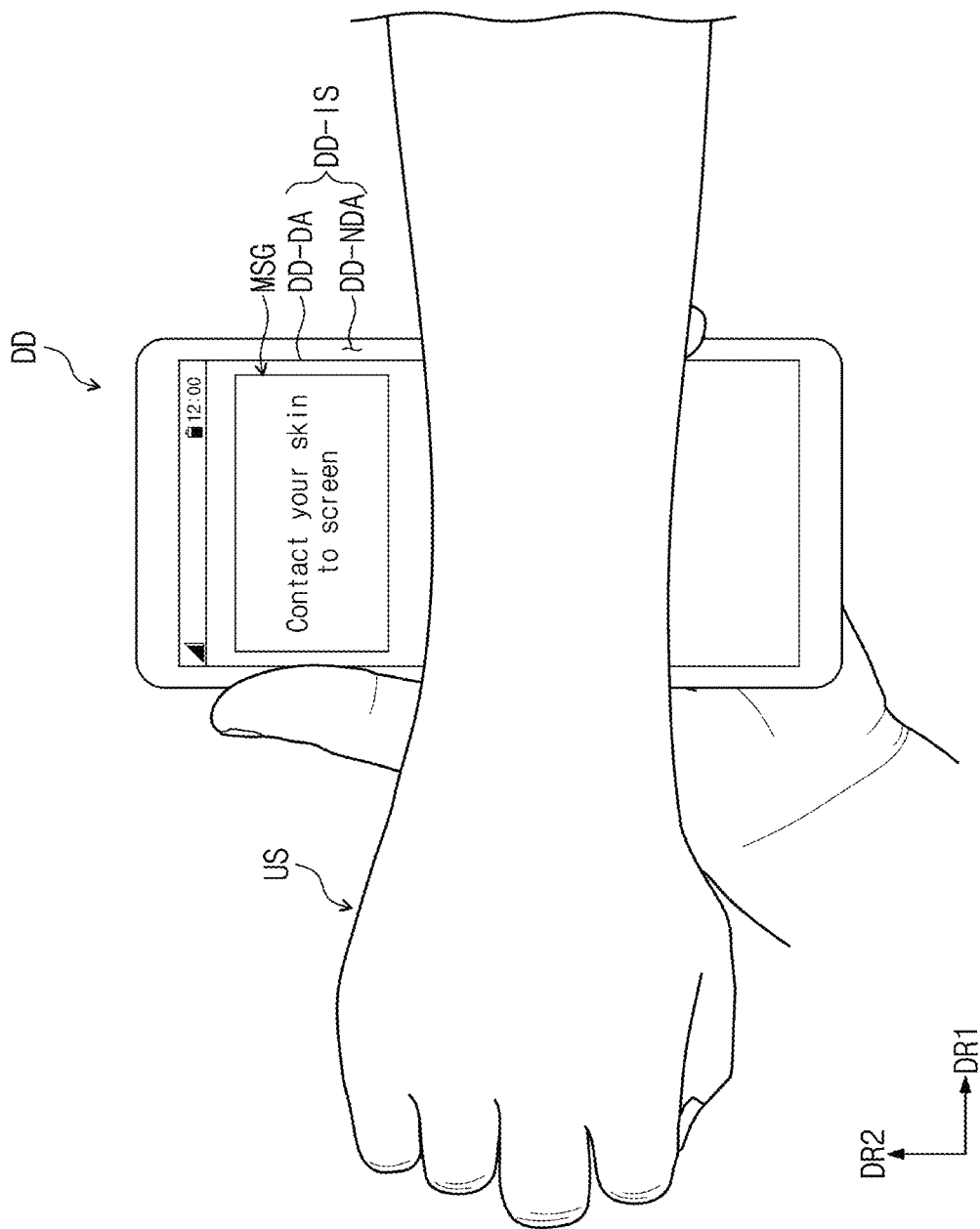
FIG. 8 is a view illustrating that a user measures a skin condition by using a display device, according to an embodiment.

FIG. 8 is a view illustrating that a user measures a skin condition by using a display device, according to an embodiment.

As illustrated in FIG. 8, in a skin measurement mode, the display device DD may display a message MSG indicating the start of the skin measurement mode on the image area DD-DA of the display surface DD-IS. A user US identifies the message MSG while holding the display device DD with his/her one hand, and touches the skin of a portion, which is to be measured, in his/her body to the image area DD-DA of the display device DD. In an embodiment, as shown in FIG. 8, the user US may touch his/her arm to the image area DD-DA of the display device DD. FIG. 8 shows that the user US measures the moisture level for the inner portion of the wrist of his/her arm, but the present disclosure is not limited thereto. A location where the user US wants to measure the skin moisture level may be various, for example, a face, a leg, an abdomen, or the like.

The display device DD may measure the moisture level of an area contacted by the user US and then may display a result of measuring the moisture level.

When the skin of the body contacts the display surface DD-IS, a capacity is changed due to a difference in permittivity between air and moisture in the skin. The display device DD may measure the amount of moisture in the skin by detecting the change amount of the capacity.

As shown in FIGS. 6 and 8, when a large area of the skin of the user US contacts the display surface DD-IS, the number of the reception electrodes RE1 to RE14 simultaneously capacitively-coupled to one transmission electrode (e.g., TE1) may be two or more. In this case, it may be difficult to accurately measure a body composition. In detail, as a contact area where the skin of the user US contacts the display surface DD-IS increases, a noise component may be included in the received signal.

Figure 9:
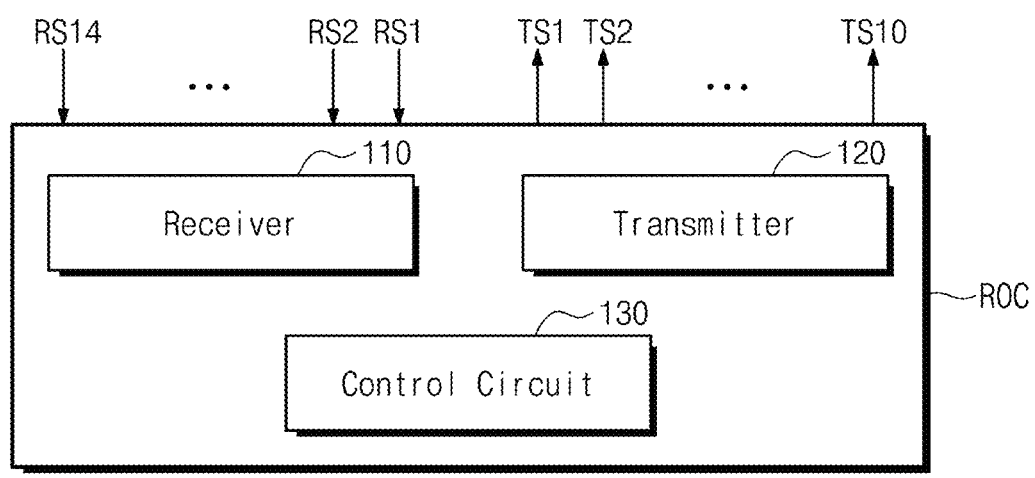
FIG. 9 is a block diagram illustrating a readout circuit, according to an embodiment.

FIG. 9 is a block diagram illustrating a readout circuit, according to an embodiment.

Referring to FIGS. 6 and 9, the readout circuit ROC includes a receiver 110, a transmitter 120, and a control circuit 130.

The receiver 110 receives first to fourteenth reception signals RS1 to RS14 from the first to fourteenth reception electrodes RE1 to RE14. The first to fourteenth reception signals RS1 to RS14 received from the first to fourteenth reception electrodes RE1 to RE14 may be analog capacity signals generated by the contact of the user US (refer to FIG. 8). The receiver 110 may include an analog front end (AFE) circuit for detecting an analog capacity signal.

The transmitter 120 transmits first to tenth transmission signals TS1 to TS10 to the first to tenth transmission electrodes TE1 to TE10 in response to the control from the control circuit 130.

The readout circuit ROC may control the first to tenth transmission signals TS1 to TS10 and the first to fourteenth reception signals RS1 to RS14 depending on an operating mode. In an embodiment, the readout circuit ROC may sequentially activate the first to tenth transmission signals TS1 to TS10 provided to the first to tenth transmission electrodes TE1 to TE10. The readout circuit ROC may simultaneously receive the first to fourteenth reception signals RS1 to RS14 from the first to fourteenth reception electrodes RE1 to RE14.

In an embodiment, the readout circuit ROC may simultaneously provide the first to tenth transmission electrodes TE1 to TE10 with the first to tenth transmission signals TS1 to TS10, each of which has an active level. The readout circuit ROC may sequentially receive the first to fourteenth reception signals RS1 to RS14 from the first to fourteenth reception electrodes RE1 to RE14.

Figure 10:
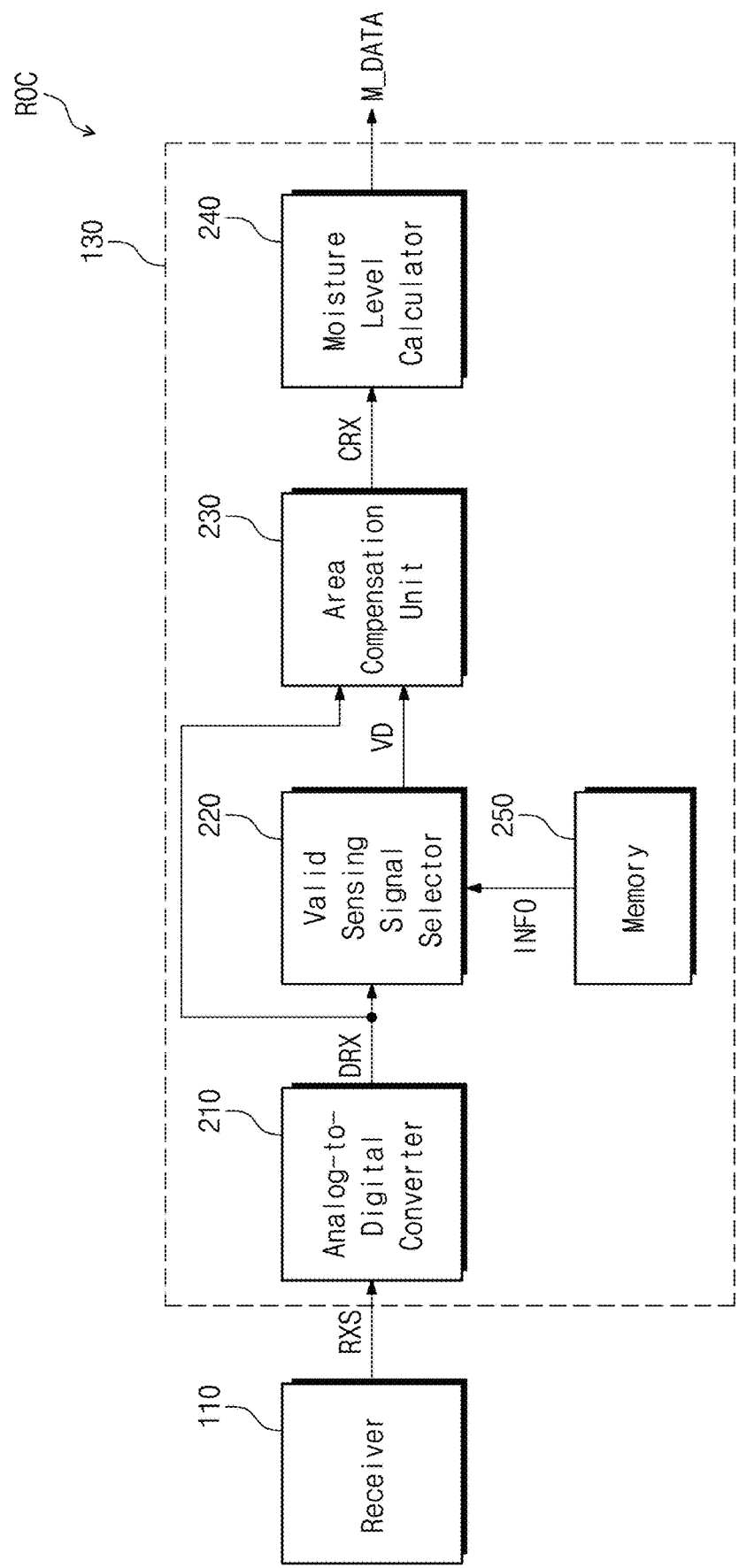
FIG. 10 is a block diagram illustrating a configuration of a control circuit in a readout circuit, according to an embodiment.

FIG. 10 is a block diagram illustrating a configuration of the control circuit 130 in the readout circuit ROC, according to an embodiment.

Referring to FIG. 10, the control circuit 130 in the readout circuit ROC may include an analog-to-digital converter 210, a valid sensing signal selector 220, an area compensation unit 230, a moisture level calculator 240, and a memory 250.

The analog-to-digital converter 210 may receive sensing signals RXS from the receiver 110. The sensing signals RXS may be analog capacity signals caused by a touch of the user US (refer to FIG. 8). The sensing signals RXS may include the first to fourteenth reception signals RS1 to RS14 shown in FIG. 9. The analog-to-digital converter 210 converts the sensing signals RXS into digital sensing signals DRX.

The memory 250 includes area information INFO of the input sensor ISU.

The valid sensing signal selector 220 divides the input sensor ISU (refer to FIG. 6) into a plurality of blocks based on the area information INFO from the memory 250, and then selects valid sensing blocks among the plurality of blocks based on the digital sensing signals DRX from the analog-to-digital converter 210. The valid sensing signal selector 220 provides the area compensation unit 230 with valid sensing signals VD, which correspond to valid sensing blocks, from among the digital sensing signals DRX received from the analog-to-digital converter 210.

In an embodiment, it is illustrated and described that the valid sensing signal selector 220 receives the area information INFO of the input sensor ISU from the memory 250 in the control circuit 130, but the present disclosure is not limited thereto. In an embodiment, the control circuit 130 may not include the memory 250. In this case, the valid sensing signal selector 220 may receive the area information INFO of the input sensor ISU from a main controller (not shown). Herein, the main controller may be a processor that controls operations of the panel driving circuit PDC and the readout circuit ROC shown in FIG. 2.

The area compensation unit 230 calculates a touch area based on the digital sensing signals DRX received from the analog-to-digital converter 210. The area compensation unit 230 performs capacitance compensation according to the touch area on the valid sensing signals VD received from the valid sensing signal selector 220 and then outputs compensation signals CRX. The touch area may be proportional to the number of the digital sensing signals DRX, each of which has a signal level that is not less than a reference value, from among the digital sensing signals DRX.

The moisture level calculator 240 outputs a moisture level signal M_DATA indicating a moisture level of the user US (refer to FIG. 8) based on the compensation signals CRX.

Figure 11:
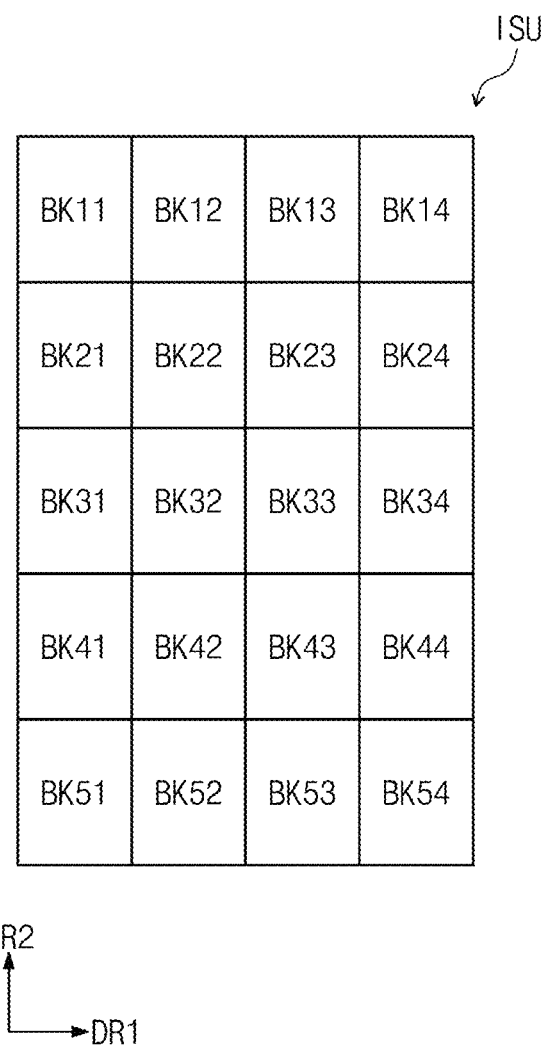
FIG. 11 is a diagram for describing an operation of a valid sensing signal selector shown in FIG. 10.

FIG. 11 is a diagram for describing an operation of the valid sensing signal selector 220 shown in FIG. 10.

Referring to FIGS. 10 and 11, the valid sensing signal selector 220 divides the input sensor ISU (refer to FIG. 6) into blocks BK11 to BK14, BK21 to BK24, BK31 to BK34, BK41 to BK44, and BK51 to BK54 based on the area information INFO from the memory 250. In FIG. 11, the input sensor ISU is divided into 20 blocks, but the present disclosure is not limited thereto. In an embodiment, the valid sensing signal selector 220 may determine the number of blocks in the first direction DR1 and the number of blocks in the second direction DR2 in consideration of the number of the transmission electrodes TE1 to TE10 of the input sensor ISU included in the area information INFO, the number of the reception electrodes RE1 to RE14 of the input sensor ISU included in the area information INFO, a size (or area) of each of the transmission electrodes TE1 to TE10 and a size (or area) of each of the reception electrodes RE1 to RE14, or the like.

Figure 12:
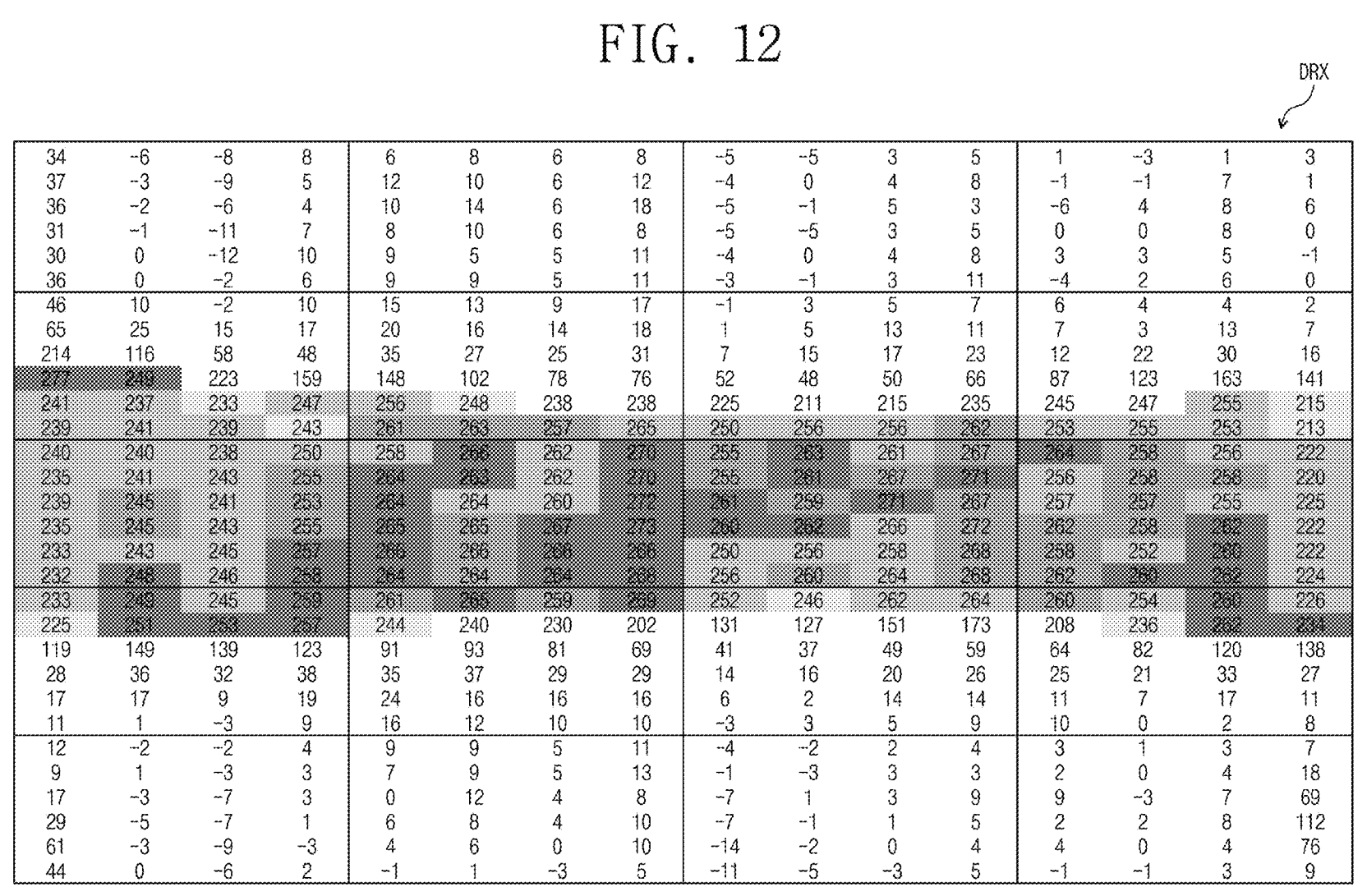

FIG. 12 is a diagram illustrating a part of the digital sensing signals DRX output from the analog-to-digital converter 210 illustrated in FIG. 10.

Numbers shown in FIG. 12 are the digital sensing signals DRX obtained as the analog-to-digital converter 210 converts the sensing signals RXS received from the reception electrodes RE1 to RE14 shown in FIG. 6 through the receiver 110 into digital signals. The numbers shown in FIG. 12 are only examples, and the embodiments described herein are not limited thereto.

In the example shown in FIG. 8, a body (i.e., an arm) of the user US has contacted a middle portion of the display device DD in parallel with the first direction DR1. The digital sensing signals DRX may have various values depending on an extent to which the arm of the user US contacts the input sensor ISU.

In an embodiment, when the arm of the user US is in close contact with the transmission electrodes TE1 to TE10 and the reception electrodes RE1 to RE14, the digital sensing signals DRX is a high value (e.g., 200 or more). When the arm of the user US is in weak contact with the transmission electrodes TE1 to TE10 and the reception electrodes RE1 to RE14, the digital sensing signals DRX is an intermediate value (e.g., 20 or more and 200 or less). When the arm of the user US does not contact the transmission electrodes TE1 to TE10 and the reception electrodes RE1 to RE14, the digital sensing signals DRX is a low value (e.g., 20 or less).

However, as well as information about an event that the arm of the user US contacts the transmission electrodes TE1 to TE10 and the reception electrodes RE1 to RE14, an intrinsic characteristic of each of the transmission electrodes TE1 to TE10 and the reception electrodes RE1 to RE14 may also affect the digital sensing signals DRX. As described above, when the body of the user US is positioned close to the first to tenth transmission electrodes TE1 to TE10 and the first to fourteenth reception electrodes RE1 to RE14, mutual capacitances between the first to tenth transmission electrodes TE1 to TE10 and the first to fourteenth reception electrodes RE1 to RE14 are changed. There is a difference in a capacitance change amount between the first to tenth transmission electrodes TE1 to TE10 and the first to fourteenth reception electrodes RE1 to RE14. When there is a need for only touch location information of the user US, the difference in the capacitance change amount may not particularly matter. However, the capacitance difference may affect a result of measuring a skin moisture level.

Referring to FIGS. 10, 11 and 12, the valid sensing signal selector 220 divides the input sensor ISU into blocks BK11 to BK14, BK21 to BK24, BK31 to BK34, BK41 to BK44, and BK51 to BK54 and searches for valid sensing blocks.

The valid sensing signal selector 220 may classify the digital sensing signals DRX having an intermediate value or a low value from among the digital sensing signals DRX as noise, and then may only regard the digital sensing signals DRX having a high value (e.g. 200 or more) as valid data. In an embodiment, the valid sensing signal selector 220 may regard the digital sensing signals DRX higher than a reference value (e.g. 200 or more) from among the digital sensing signals DRX as valid data.

In the example shown in FIGS. 11 and 12, the valid sensing signal selector 220 may select blocks BK31, BK32, BK33, and BK34 including valid data.

The valid sensing signal selector 220 searches for a representative value of each of the selected blocks BK31, BK32, BK33, and BK34. The representative value may be one of a mean, a mode, or a median of the digital sensing signals DRX of each block.

Figure 13:
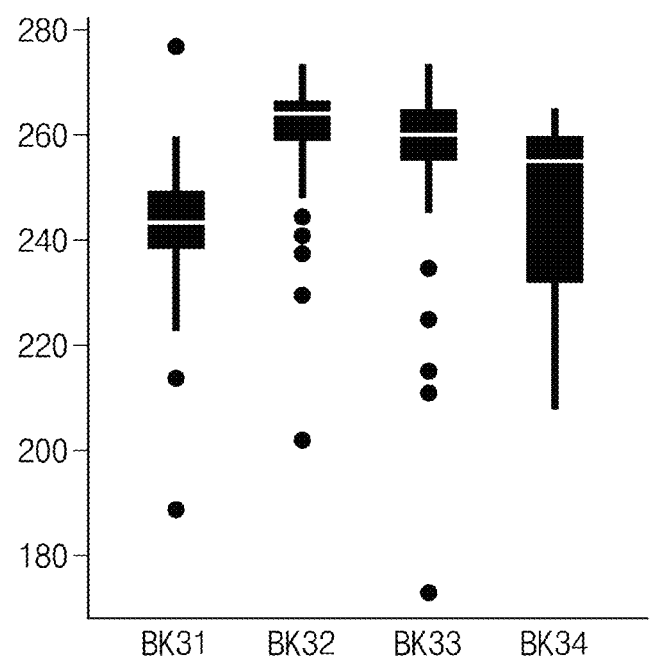
FIG. 13 is a diagram illustrating a median of each of selected blocks.

FIG. 13 is a diagram illustrating a median of each of the selected blocks BK31, BK32, BK33, and BK34.

Referring to FIGS. 11, 12, and 13, the valid sensing signal selector 220 calculates intermediate values of the digital sensing signals DRX of each of the blocks BK31, BK32, BK33, and BK34. The intermediate values of the blocks BK31, BK32, BK33, and BK34 may be 243, 264, 260 and 255.

The valid sensing signal selector 220 calculates a mean of 255.5 among the intermediate values of the blocks BK31, BK32, BK33, and BK34, and then calculates a difference value between the mean and the intermediate values of the blocks BK31, BK32, BK33, and BK34. The difference value may be expressed as an absolute value. The difference values of the blocks BK31, BK32, BK33, and BK34 are 12.5, 8.5, 4.5, and 0.5, respectively.

The valid sensing signal selector 220 selects, as valid sensing blocks, the remaining blocks BK32, BK33, and BK34 other than the block BK31 corresponding to the largest value among the difference values of the blocks BK31, BK32, BK33, and BK34. The valid sensing signal selector 220 outputs the digital sensing signals DRX of valid sensing blocks BK32, BK33, and BK34 to the area compensation unit 230 as a valid sensing signal VD.

The area compensation unit 230 regards the digital sensing signals DRX having a value higher than a reference value (e.g., 200 or more) from among the digital sensing signals DRX from the analog-to-digital converter 210 as valid data and then calculates an area (i.e., a touch area) where valid data is positioned in the input sensor ISU. In an embodiment, when the number of valid data is 'N' and the area corresponding to a piece of valid data is 'A', the touch area may be calculated as "N×A".

In general, as the touch area where the user's body US (FIG. 8) contacts the input sensor ISU increases, the capacitance between the first to tenth transmission electrodes TE1 to TE10 and the first to fourteenth reception electrodes RE1 to RE14 increases. The area compensation unit 230 compensates for the valid sensing signal VD by using a compensation value proportional to the touch area, and then outputs the compensation signal CRX.

The moisture level calculator 240 outputs the moisture level signal M_DATA based on the compensation signal CRX. The moisture level calculator 240 may select a moisture level calculation formula depending on a location (e.g., a face, an arm, an abdomen, or the like) of a skin that the user US desires to measure. Furthermore, the moisture level calculation formula may be selected depending on a gender (e.g., female or male) of the user US. In an embodiment, the moisture level signal M_DATA may be output as a value between 0 and 100.

As described above, the readout circuit ROC excludes the block BK31 having a large difference from the mean from among the blocks BK31, BK32, BK33, and BK34 including valid data from the moisture level calculation. Even though the user US (refer to FIG. 8) is in close contact with the transmission electrodes TE1 to TE10 and the reception electrodes RE1 to RE14, the block BK31 may be regarded as a block having a large capacitance difference between the first to tenth transmission electrodes TE1 to TE10 and the first to fourteenth reception electrodes RE1 to RE14. That is, the capacitance characteristic of the block BK31 may be regarded to be different from each capacitance characteristic of the blocks BK32, BK33, and BK34, each of which has a different characteristic between the first to tenth transmission electrodes TE1 to TE10 and the first to fourteenth reception electrodes RE1 to RE14.

Accordingly, it is possible to prevent a result of measuring a moisture level from being distorted by intrinsic characteristics of the input sensor ISU. Therefore, the reliability of the moisture level measurement result of the display device DD may be improved.

Figure 14:
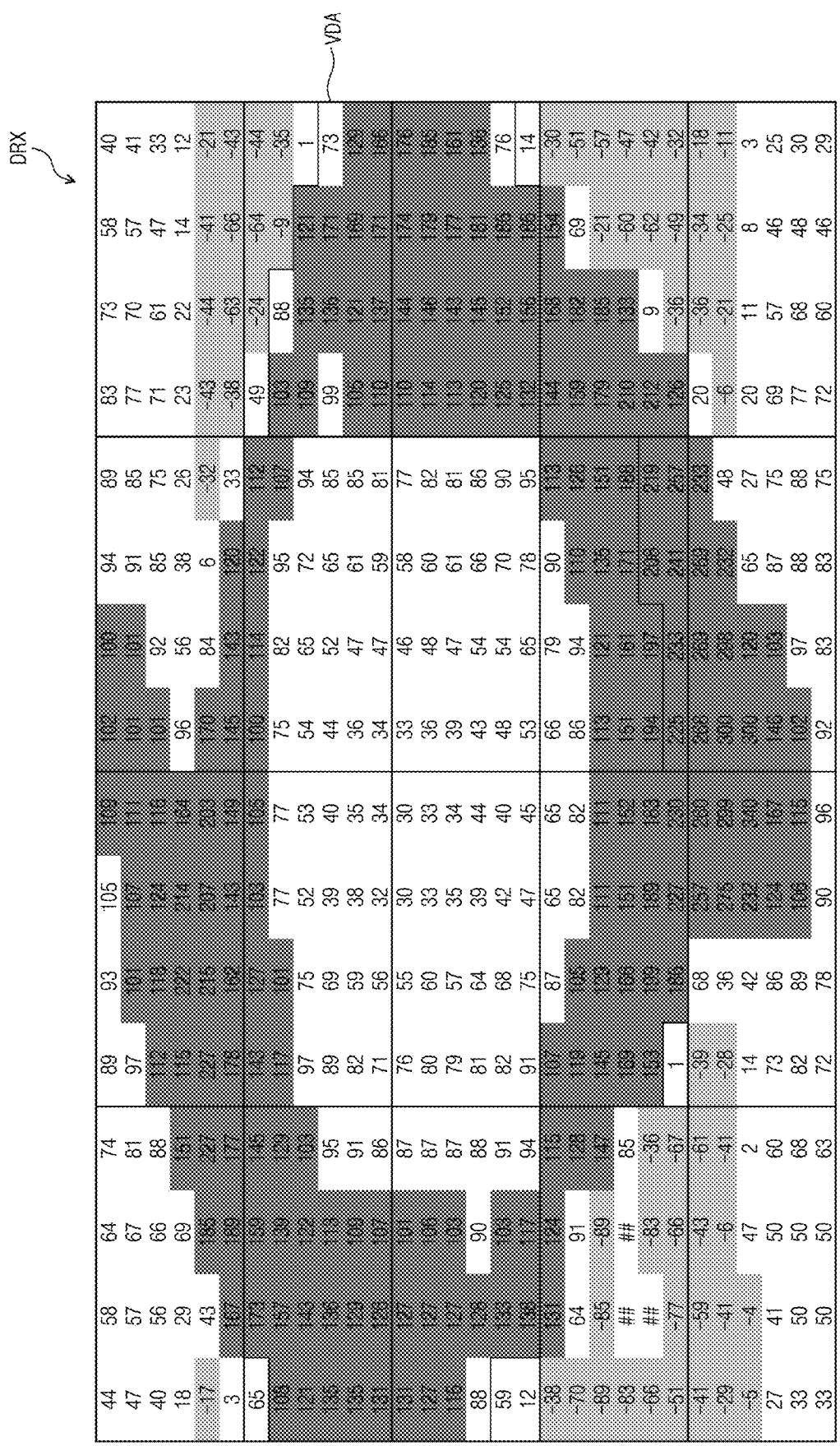
FIG. 14 is a diagram illustrating a part of digital sensing signals output from an analog-to-digital converter illustrated in FIG. 10 when a user's face contacts an input sensor.

FIG. 14 is a diagram illustrating a part of the digital sensing signals DRX output from the analog-to-digital converter 210 illustrated in FIG. 10 when a user's face contacts an input sensor.

Numbers in FIG. 14 are the digital sensing signals DRX obtained as the analog-to-digital converter 210 converts the sensing signals RXS received from the reception electrodes RE1 to RE14 shown in FIG. 6 through the receiver 110 into digital signals.

Because a user's face is more curved than another body portion, an extent (i.e., the digital sensing signals DRX) to which the face contacts the input sensor ISU may have various values. Moreover, several blocks of the blocks BK11 to BK14, BK21 to BK24, BK31 to BK34, BK41 to BK44, and BK51 to BK54 of the input sensor ISU shown in FIG. 11 may include valid data.

In an embodiment, the valid sensing signal selector 220 may determine the blocks BK21 to BK24, BK31 to BK34, and BK41 to BK44 as blocks including valid data. As described with reference to FIGS. 11 to 13, the valid sensing signal selector 220 may select valid blocks among the blocks BK21 to BK24, BK31 to BK34, and BK42 to BK43 by using a representative value of each of the blocks BK21 to BK24, BK31 to BK34, and BK41 to BK44.

The valid sensing signal selector 220 may provide the area compensation unit 230 with the digital sensing signals DRX in a valid area VDA as the valid sensing signal VD other than the digital sensing signals DRX, which has a large difference from the representative value of each of the valid blocks BK21 to BK24, BK31 to BK34, and BK42 to BK43.

An event that the valid sensing signal selector 220 selects the valid area VDA may be achieved by using an artificial intelligence algorithm.

Figure 15:
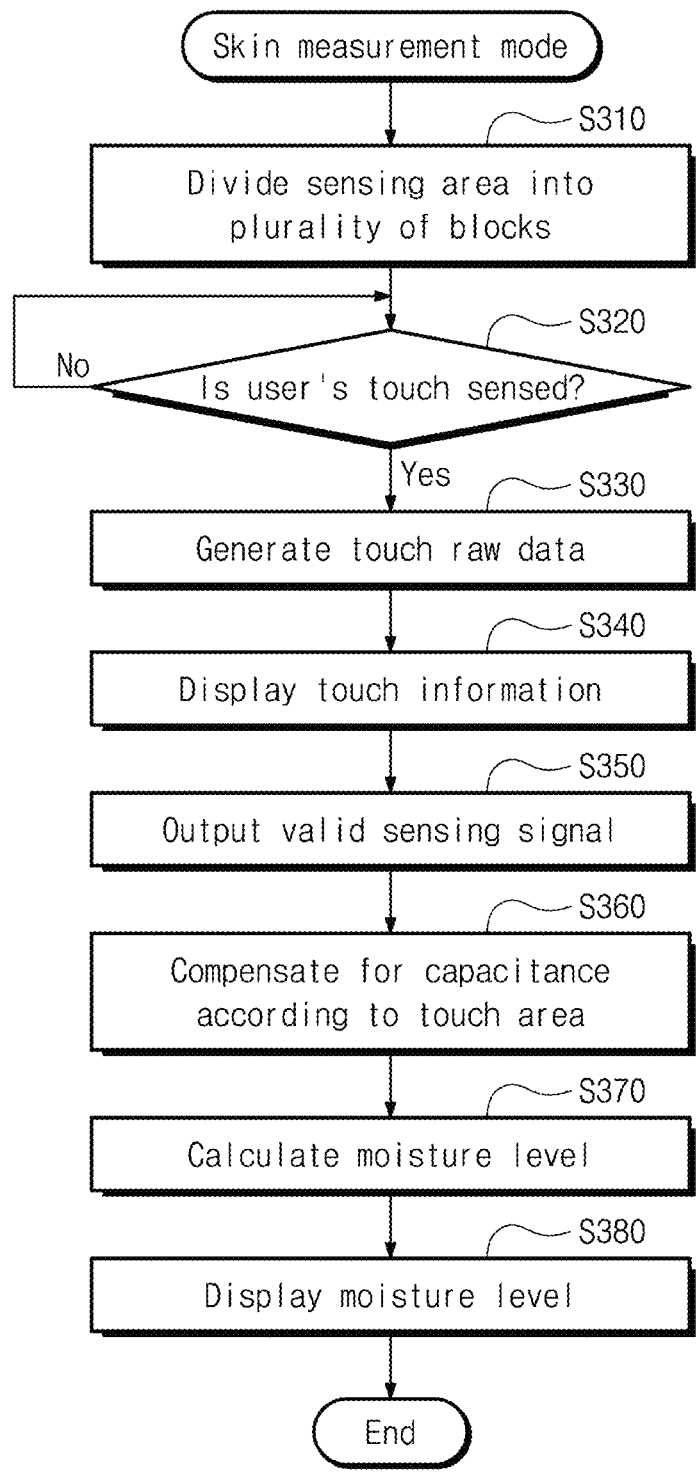
FIG. 15 is a flowchart illustrating an operation of a display device, according to an embodiment.

FIG. 15 is a flowchart illustrating an operation of a display device, according to an embodiment.

For better understanding, an operation of the display device shown in FIG. 15 will be described with reference to the readout circuit shown in FIG. 10. However, an operating method of the display device according to an embodiment is not limited to the readout circuit shown in FIG. 10.

Referring to FIGS. 8, 10, and 15, in a skin measurement mode, the display device DD may display a message MSG indicating the start of the skin measurement mode on the image area DD-DA of the display surface DD-IS.

In the skin measurement mode, the valid sensing signal selector 220 divides the input sensor ISU (refer to FIG. 6) into a plurality of blocks based on the area information INFO from the memory 250 (operation S310). In an embodiment, as illustrated in FIG. 11, the valid sensing signal selector 220 may divide the input sensor ISU into the blocks BK11 to BK14, BK21 to BK24, BK31 to BK34, BK41 to BK44, and BK51 to BK54, based on the area information INFO from the memory 250.

When the skin of a portion that the user US desires to measure contacts the image area DD-DA of the display device DD (operation S320), the receiver 110 provides the control circuit 130 with signals received from the first to fourteenth reception electrodes RE1 to RE14 (refer to FIG. 6) as the sensing signals RXS.

The analog-to-digital converter 210 in the control circuit 130 converts the sensing signals RXS to the digital sensing signals DRX. The digital sensing signals DRX output from the analog-to-digital converter 210 may be raw data for a user's touch. That is, the analog-to-digital converter 210 outputs touch raw data (operation S330).

The panel driving circuit PDC (refer to FIG. 2) may receive the touch raw data (i.e., the digital sensing signals DRX) output from the analog-to-digital converter 210 and then may display touch information on the display panel DP (operation S340).

The panel driving circuit PDC may display information indicating a touch location of the user US as graphic information in the image area DD-DA of the display device DD shown in FIG. 8.

Referring to FIGS. 10 and 15, the valid sensing signal selector 220 selects blocks including valid data from among the blocks BK11 to BK14, BK21 to BK24, BK31 to BK34, BK41 to BK44, and BK51 to BK54 and then selects valid sensing blocks from among the selected blocks.

In an embodiment, as described with reference to FIGS. 11 to 13, the valid sensing signal selector 220 selects the blocks BK31, BK32, BK33, and BK34 including valid data from among the blocks BK11 to BK14, BK21 to BK24, BK31 to BK34, BK41 to BK44, and BK51 to BK54. Besides, the blocks BK32, BK33, and BK34 among the blocks BK31, BK32, BK33, and BK34 may be selected as valid sensing blocks.

The valid sensing signal selector 220 outputs the digital sensing signals DRX of valid sensing blocks BK32, BK33, and BK34 as the valid sensing signal VD (operation S350).

The area compensation unit 230 calculates a touch area of the valid sensing blocks from among the blocks BK31, BK32, BK33, and BK34 including valid data and then compensates for the capacitance of the valid sensing signal VD depending on the touch area (operation S360). The area compensation unit 230 outputs the compensation signal CRX obtained by compensating for the capacitance.

The moisture level calculator 240 calculates a moisture level based on the compensation signal CRX and outputs the moisture level signal M_DATA (operation S370).

The panel driving circuit PDC (refer to FIG. 2) may receive the moisture level signal M_DATA output from the moisture level calculator 240, and may display moisture level information on the display panel DP (operation S380).

Figure 16:
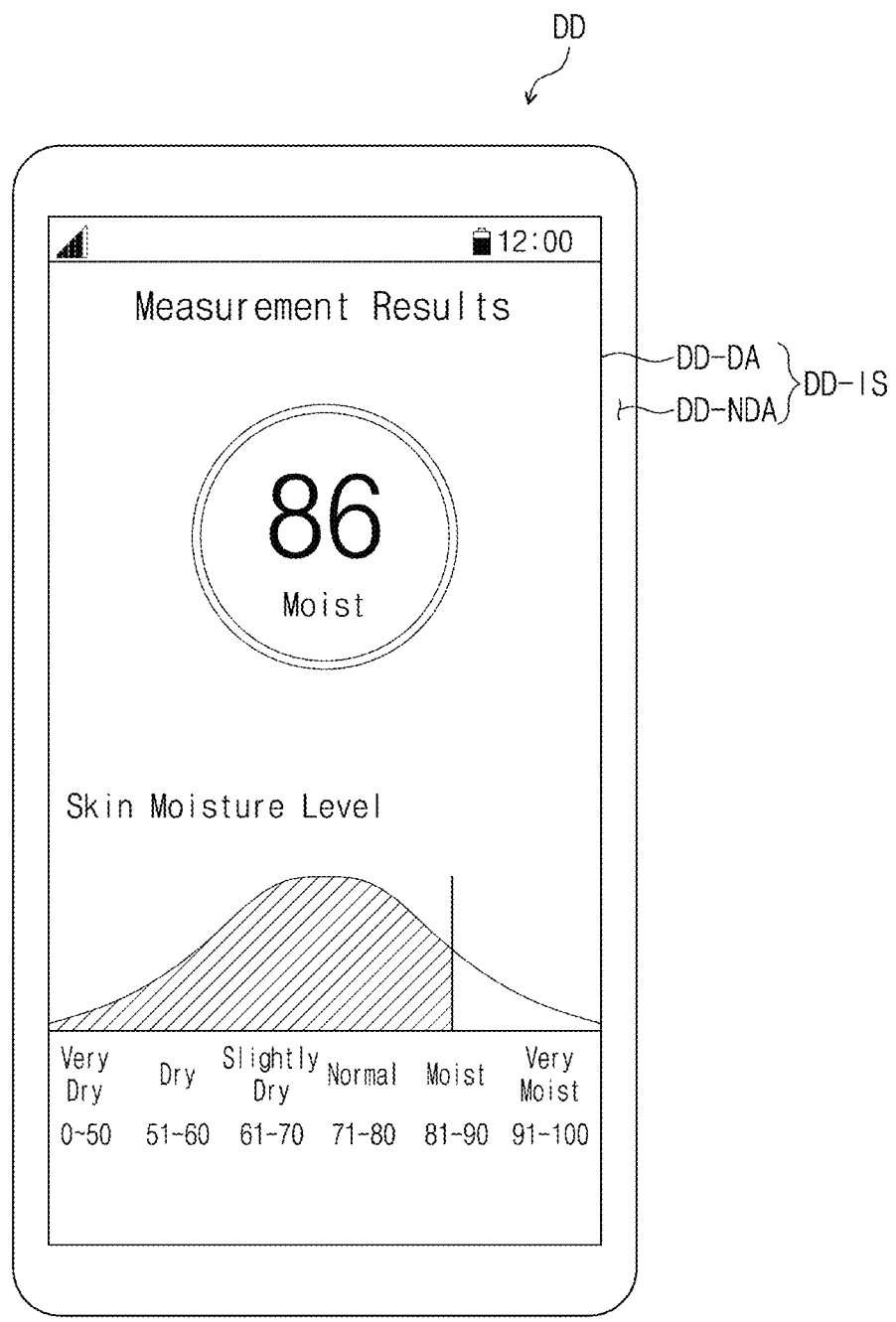
FIG. 16 is a view illustrating a result of measuring a moisture level, according to an embodiment.

FIG. 16 is a view illustrating a result of measuring a moisture level, according to an embodiment.

Referring to FIGS. 10 and 16, the display device DD may display an image corresponding to the moisture level signal M_DATA output from the readout circuit ROC in the image area DD-DA.

In an embodiment, the readout circuit ROC may provide the moisture level signal M_DATA to the panel driving circuit PDC (refer to FIG. 2). Under the control of the panel driving circuit PDC, an image corresponding to the moisture level signal M_DATA is displayed in the active area AA of the display panel DP (refer to FIG. 5). The image displayed in the active area AA of the display panel DP may be displayed in the image area DD-DA of the display device DD. A user may easily know his/her skin moisture level through an image displayed on the display device DD.

A display device having such a configuration may measure a user's skin moisture level and may display the measurement result on a display panel. Accordingly, when a user employs the display device, the user's convenience may be improved.

In detail, when an area where the user's skin contacts an input sensor is large, it is possible to minimize an error according to a characteristic difference of the input sensor and an error according to a contact state between the user's skin and the input sensor, thereby improving the reliability of a result of measuring the user's skin moisture level.

Although certain embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A display device comprising:
    a display panel;
    an input sensor disposed on the display panel; and
    a readout circuit configured to receive sensing signals from the input sensor and to output a moisture level signal during a skin measurement mode,
    wherein the readout circuit includes:
        an analog-to-digital converter configured to convert the sensing signals into digital sensing signals;
        a valid sensing signal selector configured to divide the input sensor into a plurality of blocks, select a valid sensing block among the plurality of blocks based on the digital sensing signals and area information of the input sensor, and to output a valid sensing signal based on the sensing signals from the valid sensing block; and
        a calculator configured to output the moisture level signal based on the valid sensing signal and the digital sensing signal,
    wherein the valid sensing signal selector is configured to:
        select touch blocks, from each of which a touch of a user is detected, from among the plurality of blocks;
        calculate a representative value of each of the touch blocks and a mean of representative values of the touch blocks; and
        select the valid sensing block based on the representative values of the touch blocks and the mean.

2. The display device of claim 1, wherein the calculator includes:
    an area compensation unit configured to calculate a touch area based on the digital sensing signals and to output a compensation signal obtained by performing capacitance compensation according to the touch area on the valid sensing signal; and
    a moisture level calculator configured to output the moisture level signal based on the compensation signal.

3. The display device of claim 2, wherein the representative value is one of a mean, a median, and a mode of the compensation signal in the valid sensing block.

4. The display device of claim 1, wherein the valid sensing signal selector selects one of the touch blocks which has a greatest difference value between the mean and the respective representative values of the touch blocks, as the valid sensing block.

5. The display device of claim 1, further comprising:
    a memory configured to store the area information of the input sensor.

6. The display device of claim 2, wherein the input sensor is disposed on the display panel, and
    wherein the input sensor includes:
        first sensing electrodes;
        second sensing electrodes crossing the first sensing electrodes;
        first signal lines respectively connected to the first sensing electrodes; and
        second signal lines respectively connected to the second sensing electrodes.

7. The display device of claim 6, wherein the readout circuit is configured to transmit a transmission signal to the first signal lines and to receive the sensing signals from the second signal lines.

8. The display device of claim 6, wherein the first sensing electrodes and the second sensing electrodes are arranged in a mesh shape.

9. The display device of claim 6, wherein the readout circuit includes:
    a transmitter configured to provide transmission signals to the first signal lines;
    a receiver configured to receive the sensing signals from the second signal lines; and
    a control circuit configured to control the transmitter and the receiver and which includes the analog-to-digital converter, the valid sensing signal selector, the area compensation unit, and the moisture level calculator.

10. The display device of claim 6, wherein each of the sensing signals is representative of a capacity between one of the first sensing electrodes and one of the second sensing electrodes.

11. The display device of claim 1, wherein the touch area is proportional to a number of digital sensing signals, each of which exceeds a reference level, from among the digital sensing signals output from the analog-to-digital converter.

12. A display device comprising:
    a display panel configured to display an image;
    an input sensor disposed on the display panel and which includes first sensing electrodes and second sensing electrodes electrically isolated from the first sensing electrodes; and
    a readout circuit connected to the input sensor,
    wherein the readout circuit is configured to:
        divide the input sensor into a plurality of blocks;
        select a valid sensing block based on sensing signals received from the first sensing electrodes of the plurality of blocks; and
        output a moisture level signal based on the sensing signals from the valid sensing block,
    wherein the readout circuit comprises:
        an analog-to-digital converter configured to convert the sensing signals into digital sensing signals;
        a valid sensing signal selector configured to select the valid sensing block among the plurality of blocks based on the digital sensing signals and area information and to output a valid sensing signal based on the sensing signals from the valid sensing block;
        an area compensation unit configured to calculate a touch area based on the digital sensing signals and to output a compensation signal obtained by performing capacitance compensation according to the touch area on the valid sensing signal; and
        a moisture level calculator configured to output the moisture level signal based on the compensation signal,
    wherein the valid sensing signal selector is configured to:
        select touch blocks, from each of which a touch of a user is detected, from among the plurality of blocks;
        calculate a representative value of each of the touch blocks and a mean of representative values of the plurality of touch blocks; and
        select the valid sensing block based on the representative values of the plurality of touch blocks and the mean.

13. The display device of claim 12, wherein the representative value is one of a mean, a median, and a mode of the compensation signal in the valid sensing block.

14. An operating method of a display device including a display panel and an input sensor, the method comprising:
    dividing the input sensor into a plurality of blocks;
    receiving sensing signals from the input sensor;
    generating touch raw data based on the sensing signals;

selecting a valid sensing block among the plurality of blocks based on the touch raw data and outputting the touch raw data of the valid sensing block as a valid sensing signal;

calculating a touch area based on the touch raw data and outputting a compensation signal obtained by compensating for capacitance of the valid sensing signal depending on the touch area;

outputting a moisture level signal based on the compensation signal; and displaying an image corresponding to the moisture level signal on the display panel, wherein the selecting of the valid sensing signal includes:
- selecting touch blocks, from each of which a touch of a user is detected, from among the plurality of blocks;
- calculating a representative value of each of the touch blocks and a mean of representative values of the touch blocks;
- selecting the valid sensing block based on the representative values of the touch blocks and the mean; and
- outputting the touch raw data of the valid sensing block as the valid sensing signal.

15. The method of claim 14, wherein the representative value is one of a mean, a median, and a mode of the compensation signal in the valid sensing block.

16. The method of claim 14, wherein the input sensor is disposed on the display panel, and wherein the input sensor includes:
- first sensing electrodes;
- second sensing electrodes crossing the first sensing electrodes;
- first signal lines respectively connected to the first sensing electrodes; and
- second signal lines respectively connected to the second sensing electrodes.

* * * * *